(12) United States Patent
Monjo Cabrer et al.

(10) Patent No.: US 9,849,212 B2
(45) Date of Patent: Dec. 26, 2017

(54) IMPLANTS FOR INDUCING SOFT AND HARD TISSUE INTEGRATION

(71) Applicant: NUMAT BIOMEDICAL S.L., Palma de Mallorca (ES)

(72) Inventors: Marta Monjo Cabrer, Palma de Mallorca (ES); Joana María Ramis Morey, Palma de Mallorca (ES); Alba Córdoba Insensé, Palma de Mallorca (ES); María Satué Sahún, Palma de Mallorca (ES); Manuel Gómez Florit, Palma de Mallorca (ES)

(73) Assignee: NUMAT BIOMEDICAL S.L., Palma de Mallorca (ES)

( * ) Notice: Subject to any disclaimer, the term of this patent is extended or adjusted under 35 U.S.C. 154(b) by 0 days.

(21) Appl. No.: 14/785,253

(22) PCT Filed: Apr. 18, 2013

(86) PCT No.: PCT/EP2013/058116
§ 371 (c)(1),
(2) Date: Oct. 16, 2015

(87) PCT Pub. No.: WO2014/169959
PCT Pub. Date: Oct. 23, 2014

(65) Prior Publication Data
US 2016/0082147 A1    Mar. 24, 2016

(51) Int. Cl.
*A61L 27/06* (2006.01)
*A61L 27/04* (2006.01)
(Continued)

(52) U.S. Cl.
CPC ............. *A61L 27/06* (2013.01); *A61L 27/04* (2013.01); *A61L 27/28* (2013.01); *A61L 27/54* (2013.01);
(Continued)

(58) Field of Classification Search
CPC ............. A61L 2400/18; A61L 2430/02; A61L 2430/12; A61L 27/04; A61L 27/06;
(Continued)

(56) References Cited

U.S. PATENT DOCUMENTS 5,356,433 A * 10/1994 Rowland .................. A61F 2/88
424/422
5,782,908 A    7/1998 Cahalan et al.
(Continued)

OTHER PUBLICATIONS

McCarty (Abstract of: Med Hypotheses. 1986;19(4):345-57: 2 pages).*
(Continued)

*Primary Examiner* — Ernst V Arnold
(74) *Attorney, Agent, or Firm* — Peter B. Scull; Hamilton, DeSanctis & Cha LLP

(57) ABSTRACT

The present invention provides a biocompatible implant comprising one or more metal(s), metal alloy(s), metal oxide(s) or a combination thereof, wherein an antioxidant compound selected from the group of flavonoids or methoxytryptophols, an ester thereof, a pharmaceutically acceptable salt thereof or a combination thereof, is/are coated to at least a part of a metal, metal alloy or metal oxide surface of said biocompatible implant. This implant is useful for replace bone tissue in vertebrate animals, and furthermore restore the normal function of said tissue, mainly due to its ability of induce osseointegration and soft tissue attachment.

20 Claims, 20 Drawing Sheets

(51) Int. Cl.
| | |
|---|---|
| A61L 27/28 | (2006.01) |
| A61L 27/54 | (2006.01) |
| A61L 31/02 | (2006.01) |
| A61L 31/08 | (2006.01) |
| A61L 31/16 | (2006.01) |

(52) U.S. Cl.
CPC ............. *A61L 31/022* (2013.01); *A61L 31/08* (2013.01); *A61L 31/16* (2013.01); *A61L 2400/18* (2013.01); *A61L 2430/02* (2013.01); *A61L 2430/12* (2013.01)

(58) Field of Classification Search
CPC ........ A61L 27/28; A61L 27/54; A61L 31/022; A61L 31/08; A61L 31/16
See application file for complete search history.

(56) References Cited

U.S. PATENT DOCUMENTS

| | | | | |
|---|---|---|---|---|
| 2005/0234558 | A1* | 10/2005 | Petersson | A61L 27/56 623/23.5 |
| 2005/0239721 | A1* | 10/2005 | Rosenbloom | A61K 31/121 514/27 |
| 2008/0241211 | A1 | 10/2008 | Han et al. | |
| 2010/0068238 | A1 | 3/2010 | Managoli | |
| 2011/0004148 | A1* | 1/2011 | Ishii | A61F 2/958 604/20 |
| 2011/0112654 | A1 | 5/2011 | Faldt | |
| 2012/0121661 | A1* | 5/2012 | Schwartz | A61L 27/32 424/400 |

OTHER PUBLICATIONS

Ng et al. (J Neural Transm 2000;107:1243-1251).*
Lee et al. (Biomaterials 2005;26:1721-1730).*
Geetha et al. (Progress in Materials Science 2009;54:397-425).*
Trzeciakiewicz et al. (Nutrition Research Reviews 2009;22:68-81).*
Trivedi eta I. (Molecular and Cellular Endocrinology. 2009;302:86-91).*
Wong, Ricky W. K. et al., Effect of Naringin Collagen Graft of Bone Formation, Biomaterials, available on line Nov. 23, 2005 (www.sciencedirect.com), pp. 1824-1831, vol. 27 (2006), Elsevier, Science Direct, Amsterdam, NL.
International Search Report and Written Opinion of the International Searching Authority Search Report Application No. PCT/EP2013/058116 issued by European Patent Office, Rijswijk, NL, dated Jan. 15, 2014.
Heim, Kelly et al., Flavonoid antioxidants: chemistry, metabolism and structure-activity relationships, The Journal of Nutritional Biochemistry, Oct. 2002, pp. 572-584, vol. 13, Issue 10, Elsevier, Amsterdam, NL.
Amic, Dragan et al., SAR and QSAR of the Antioxidant Activity of Flavonoids, Current Medicinal Chemistry, Mar. 2007, pp. 827-845, vol. 14, No. 7, Bentham Science Publishers, Potomac, MD, USA.
Johansson, Carina B., et al., A Quantitative Comparison of Machined Commercially Pure Titanium and Titanium-Aluminum-Vanadium Implants in Rabbit Bone, The International Journal of Oral & Maxillofacial Implants, May 1998, vol. 13, Issue 3, pp. 315-321, Quintessence Publishing, Barcelona, Spain.
Ronold, Hans Jacob et al., The use of a coin shaped implant for direct in situ measurement of attachment strength for osseointegrating biomaterial surfaces, Biomaterials, Oct. 2001, pp. 2201-2209, Elsevier, Amsterdam, NL.
Monjo, Marta et al., Correlation between molecular signals and bone bonding to titanium implants, Clinical Oral Implants Research, Sep. 2013 (manuscript accepted Apr. 6, 2012), pp. 1035-1043, vol. 24, Issue, John Wiley & Sons Ltd, Hoboken, NJ, USA.
Gristina, Anthony G., Biomaterial-Centered Infection: Microbial Adhesion Versus Tissue Integration, Science, Sep. 25, 1987, pp. 1588-1595, vol. 237, Issue 4822, American Association for the Advancement of Science, Washington, DC, USA.
Sawyer, A.A., et al., Regulation of mesenchymal stem cell attachment and spreading on hydroxyapatite by RGD peptides and adsorbed serum proteins, Biomaterials, May 2005, pp. 1467-1475, vol. 26, Issue 13, Science Direct, Elsevier, BV, Amsterdam, NL.
Cordoba, Alba et al., Flavonoid-Modified Surfaces: Multifunctional Bioactive Biomaterials with Osteopromotive, Anti-Infl ammatory, and Anti-Fibrotic Potential, Advanced Healthcare Materials, Oct. 2014, pp. 1-10, vol. 4, Issue 4, Wiley-VCH Verlag GmbH & Co. KGaA, Weinheim, DE.
Cordoba, Alba et al., Bioinspired Quercitrin Nanocoatings: A Fluorescence-Based Method for Their Surface Quantification, and Their Effect on Stem Cell Adhesion and Differentiation to the Osteoblastic Lineage, ACS Applied Materials & Interfaces, Jul. 2015, pp. 16857-16864, vol. 7, Issue 30, American Chemical Society, New York, NY, USA.
Gomez-Florit, Manuel et al., Quercitrin-nanocoated titanium surfaces favour gingival cells against oral bacteria, Scientific Reports, Mar. 2016, pp. 1-9, vol. 6, Issue 22444, Nature Research, New York, NY, USA.

* cited by examiner

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Sense primer for amplifying COL3A1 gene

<400> SEQUENCE: 1
ggcctactgg gcctggtggt                                              20

<210> SEQ ID NO 2
<211> LENGTH: 20
```

```
<212> TYPE: DNA
<213> ORGANISM: Artificial Sequence
<220> FEATURE:
<223> OTHER INFORMATION: Antisense primer for amplifying COL3A1 gene

<400> SEQUENCE: 2
ccacgttcac caggggcacc                                                    20

<210> SEQ ID NO 3
<211> LENGTH: 20
<212> TYPE: DNA
<213> ORGANISM: Artificial Sequence
<220> FEATURE:
<223> OTHER INFORMATION: Sense primer for amplifying IL6 gene

<400> SEQUENCE: 3
aggagacttg cctggtgaaa                                                    20

<210> SEQ ID NO 4
<211> LENGTH: 19
<212> TYPE: DNA
<213> ORGANISM: Artificial Sequence
<220> FEATURE:
<223> OTHER INFORMATION: Antisense primer for amplifying IL6 gene

<400> SEQUENCE: 4
gcatttgtgg ttgggtcag                                                     19

<210> SEQ ID NO 5
<211> LENGTH: 20
<212> TYPE: DNA
<213> ORGANISM: Artificial Sequence
<220> FEATURE:
<223> OTHER INFORMATION: Sense primer for amplifying b-Actin gene

<400> SEQUENCE: 5
ctggaacggt gaaggtgaca                                                    20

<210> SEQ ID NO 6
<211> LENGTH: 23
<212> TYPE: DNA
<213> ORGANISM: Artificial Sequence
<220> FEATURE:
<223> OTHER INFORMATION: Antisense primer for amplifying b-Actin gene

<400> SEQUENCE: 6
aagggacttc ctgtaacaat gca                                                23

<210> SEQ ID NO 7
<211> LENGTH: 20
<212> TYPE: DNA
<213> ORGANISM: Artificial Sequence
<220> FEATURE:
<223> OTHER INFORMATION: Sense primer for amplifying GAPDH gene

<400> SEQUENCE: 7
tgcaccacca actgcttagc                                                    20

<210> SEQ ID NO 8
<211> LENGTH: 21
<212> TYPE: DNA
<213> ORGANISM: Artificial Sequence
<220> FEATURE:
<223> OTHER INFORMATION: Antisense primer for amplifying GAPDH gene

<400> SEQUENCE: 8
```

```
ggcatggact gtggtcatga g                                              21

<210> SEQ ID NO 9
<211> LENGTH: 20
<212> TYPE: DNA
<213> ORGANISM: Artificial Sequence
<220> FEATURE:
<223> OTHER INFORMATION: Sense primer for amplifying ALP gene

<400> SEQUENCE: 9
ccgctatcct ggctccgtgc                                                20

<210> SEQ ID NO 10
<211> LENGTH: 20
<212> TYPE: DNA
<213> ORGANISM: Artificial Sequence
<220> FEATURE:
<223> OTHER INFORMATION: Antisense primer for amplifying ALP gene

<400> SEQUENCE: 10
ggtgggctgg cagtggtcag                                                20

<210> SEQ ID NO 11
<211> LENGTH: 20
<212> TYPE: DNA
<213> ORGANISM: Artificial Sequence
<220> FEATURE:
<223> OTHER INFORMATION: Sense primer for amplifying Coll-1 gene

<400> SEQUENCE: 11
cctgacgcac ggccaagagg                                                20

<210> SEQ ID NO 12
<211> LENGTH: 20
<212> TYPE: DNA
<213> ORGANISM: Artificial Sequence
<220> FEATURE:
<223> OTHER INFORMATION: Antisense primer for amplifying Coll-1 gene

<400> SEQUENCE: 12
ggcagggctc gggtttccac                                                20

<210> SEQ ID NO 13
<211> LENGTH: 16
<212> TYPE: DNA
<213> ORGANISM: Artificial Sequence
<220> FEATURE:
<223> OTHER INFORMATION: Sense primer for amplifying OC gene

<400> SEQUENCE: 13
gaagcccagc ggtgca                                                    16

<210> SEQ ID NO 14
<211> LENGTH: 19
<212> TYPE: DNA
<213> ORGANISM: Artificial Sequence
<220> FEATURE:
<223> OTHER INFORMATION: Antisense primer for amplifying OC gene

<400> SEQUENCE: 14
cactacctcg ctgccctcc                                                 19

<210> SEQ ID NO 15
<211> LENGTH: 19
<212> TYPE: DNA
<213> ORGANISM: Artificial Sequence
```

```
<220> FEATURE:
<223> OTHER INFORMATION: Sense primer for amplifying Runx2 gene

<400> SEQUENCE: 15
gccttcaagg tggtagccc                                                19

<210> SEQ ID NO 16
<211> LENGTH: 20
<212> TYPE: DNA
<213> ORGANISM: Artificial Sequence
<220> FEATURE:
<223> OTHER INFORMATION: Antisense primer for amplifying Runx2 gene

<400> SEQUENCE: 16
cgttacccgc catgacagta                                               20
```

IMPLANTS FOR INDUCING SOFT AND HARD TISSUE INTEGRATION

FIELD OF THE INVENTION

The present invention relates to the field of biocompatible implants, in particular biocompatible implants comprising at least one metal such as titanium, zirconium, tantalum, hafnium, niobium, chromium-vanadium alloy and stainless steel, or an alloy thereof. More specifically, the present invention relates to biocompatible implants comprising a metal, metal alloy and/or metal oxide surface which comprise a coating providing for improved osseointegration and soft tissue attachment of said biocompatible implant when implanted into a mammalian body.

BACKGROUND OF THE INVENTION

The use of implants to restore the function of traumatized or degenerated connective tissues and thus to improve the quality of life of a patient has become widespread. The long-term success of dental implants largely depends on rapid healing with safe integration into the jaw bone and soft tissue. The integration of the dental implant intra-osseus component and the transmucosal component (abutment) with the hard (bone) and the soft (gingiva) tissue respectively, is essential in order to minimize dental implant failure.

Osseointegration is defined as the direct structural and functional connection between living bone and the surface of a load-bearing artificial implant. Current research of biomaterials is focused on inducing said physiological event by selecting a proper chemical or biological molecule able to provoke it. On the other hand, abutment surface properties may promote gingival fibroblasts attachment and synthesis of collagen-rich connective tissue, providing a tighter seal around the abutment, avoiding bacterial penetration and downgrowth of gingival epithelial cells.

Titanium (Ti) and its alloys are the materials most frequently used as bone implants as they combine good mechanical properties, such as high strength, high toughness, and low density, with good biocompatibility, caused by biological inertness due to a chemically stable surface oxide layer and an elastic modulus closer to that of bone than ceramics or steel. Ti implants are applied in various sites; in the jaw as dental implants and abutments for the bone and soft tissue respectively, as plates, screws, pins and wires to facilitate bone healing, and as prostheses for knee, hip, and other joints. Ti is commonly used in dental and orthopaedic applications but also in vascular stents.

The surface of Ti is only bioinert, thus current research on modification of implant surfaces focuses on making virtual bioinert materials become bioactive. The assortment of surface modifications ranges from non-biological coatings, such as carbide, fluorine, calcium, hydroxyl apatite or calcium phosphate, to biological coatings that bind different biomolecules to the implant surface. Such binding has often been carried out using for example chemical reactants such as formalin or glutaraldehyde, but the reactive nature of these agents often leads to the biomolecules becoming biologically inactive and/or with enhanced immunoreactivity, which is of course undesirable.

Biomolecules can be immobilized through a variety of procedures such as adsorption, covalent coupling, electrochemical surface modifications and self organized organic layers on the implant surface. It is known that oxide layers on titanium based materials show isoelectric points around 4.1 indicating that these oxide layers carry a negative charge under in vivo conditions. Thus, macromolecules positively charged under these conditions should adsorb due to electrostatic interactions.

Adsorptive binding methods combine the advantage of being simple and applicable to a nearly unlimited extent. Drawbacks are the rather low stability of biomolecule fixation, a non-defined release behaviour of biomolecules and possible conformational changes of the directly adsorbed molecules.

The advantage of covalent binding is the stable fixation of the biomolecule, combined with the chance to preserve biological activity to some degree if the molecule is combined with linkers/spacers of sufficient length. However, if more than one biomolecule is considered for immobilization, it is difficult to combine different molecules in a defined way on the surface. Thus, there is a need in the prior art to conceive covalent surface attachment strategies that are successful, with stable coatings that keep the biochemical activity of the biomolecule, in comparison with physical adsorption that is not successful for long-term implantation mainly due to the desorption of biomolecules.

As selected antioxidants, both flavonoids and methoxytryptophols have never been reported to be covalently attached to the metal surface of an implant, directly or through a linker. Moreover, methoxytryptophols have never been reported in the context of bone regeneration or implants and surface coatings for improved osseointegration and soft tissue attachment.

Flavonoids are natural phenolic compounds present in fruit and vegetables with antioxidant and many biological functions, including osteogenic, anti-osteoclastogenic and anti-adipogenic effects. Besides the osteogenic capacity of these biomolecules, another property that might be beneficial is their antimicrobial effects. Flavonoids have previously been described in US 2010/0068238A1 in the context of biocompatible medical implants, such as stents, that comprise a composition for controlled delivery of flavonoids or a derivative thereof for prevention of restenosis. However, there is no mention of the use of flavonoids for improved osseointegration or soft tissue attachment. The coating process is based on the use of bioresorbable polymers for controlled release and does not mention the use of covalent attachment for permanently binding flavonoids to the implant surface.

Furthermore, US 2011/0112654A1 discloses a bone implant coated or impregnated with flavones, which presents the ability of promoting osseointegration, as well as reducing inflammation. However, the application is based on the use of lactoferrin in dip-coated titanium implants, which can be combined with other substances including flavones, for the reduction of inflammation, increased osseointegration and reduction of adherent bacteria. Thus, it does not mention the use of covalent attachment for permanently binding flavonoids to the implant surface.

In US 2008/0241211A1 is described a medical appliance for bone regeneration that includes an osteinductive enhancer such as a flavonoid. However, the application describes the use of flavonoids in bone graft applications with demineralized bone matrix and collagen sponges, and does not describe the use of flavonoids covalently attached to implant surfaces. A similar application is described by Wong et al. in Biomaterials 27 (2006) 1824-1831 with the use of the flavonoid naringin in collagen bone grafts. Thus, a flavonoid solution is mixed with the collagen matrix and does not include the use of implant surfaces or a method for covalently binding flavonoids to metal implant surfaces.

Methoxytryptophols like 5-methoxytryptophol and 6-methoxytryptophol among others, are indole compounds that are neither a melatonin metabolite nor its precursor, and possess antioxidant properties. Their effects on bone or coated on an implant have never been reported before.

Despite the availability of biocompatible implants in the art today, there is still a need to identify alternative biocompatible implants which further may facilitate osseointegration of an implant when introduced into a mammalian body. Furthermore, there is a limitation of most of the available techniques with regards to the physical absorption (labile union) of these compounds onto the surface of the implant.

DESCRIPTION OF THE INVENTION

Surprisingly, the present invention provides an implant which overcomes the technical disadvantages of implants previously exposed. Accordingly, the present inventors have now surprisingly found that by binding a flavonoid or a methoxytryptophol, covalently or physically adsorbed, an ester thereof, and/or a pharmaceutically acceptable salt thereof and/or a combination thereof to a metal, metal alloy or metal oxide surface, such as a titanium and/or a titanium alloy surface, of a biocompatible implant, the osseointegrating and soft tissue attachment properties of the implant may be greatly facilitated. Such a biocompatible implant has not previously been known nor implied within the field.

The implant of the present invention presents an improvement of the attachment of the active biomolecule, in this case antioxidants, to the surface of the metal base. Furthermore, this attachment is improved when a linker with certain characteristics is used, and even more when a reduction of the complex linker-antioxidant is performed. This technical effect is demonstrated by showing that in implants wherein the antioxidant has been attached by covalent binding to the implant surface, the antioxidant is not released to the media (see examples 1, 2 and 3).

Furthermore, both human mesenchymal stem cells and gingival fibroblasts cultured on implants where the antioxidant has been covalently attached showed superior differentiation than cells cultured on implants where the antioxidant was simply physically attached. This surprising effect has been demonstrated by showing that genes involved in extracellular matrix production and organization and in regulation of cell adhesion, such as Collagens and Runx2, increased their expression in cells cultured on implants where the antioxidant has been covalently attached (see examples 2 and 3). This ability makes the implant of the present invention an ideal alternative in treatments where regeneration of both hard and soft tissues is required, such as in dental implants for the screws and abutments.

Additionally, the implant of the present invention is able to minimize undesired physiological effects occurred normally around the implanted zones such as inflammation. In cells cultured on implants with antioxidants covalently attached, the expression of interleukin-6 mRNA levels decreased as showed in example 2.

In a first aspect, the invention relates to a biocompatible implant comprising one or more metal(s), metal alloy(s), metal oxide(s) or a combination thereof, wherein an antioxidant compound selected from the group of flavonoids or methoxytryptophols, an ester thereof, a pharmaceutically acceptable salt thereof or a combination thereof, is/are coated to at least a part of a metal, metal alloy or metal oxide surface of said biocompatible implant.

When "at least a part of a metal, metal alloy or metal oxide surface" is referred to, this means that a metal, metal alloy, metal oxide or a combination thereof surface of an implant do not need to be fully covered by covalently bound antioxidants, but some parts of the metal, metal alloy and/or metal oxide surface may lack an antioxidant coating, contain less antioxidant and/or some parts of the metal, metal alloy and/or metal oxide surface may also comprise physically bound antioxidant in addition to the covalently bound antioxidant, e.g if remaining after the treatment of the surface to attach the antioxidant thereto. Furthermore, some parts of the surface of the implant according to the invention do not need to comprise a metal, metal alloy and/or metal oxide, but may instead comprise other materials, or combinations thereof.

In a preferred embodiment, the flavonoid compound comprises at least one carbonyl group, and more preferably those selected from quercitrin, taxifolin, galangin, diosmetin, chrysin or derivatives thereof.

In another preferred embodiment the methoxytryptophol compound is selected from 5-methoxytryptophol or 6-methoxytryptophol.

In another preferred embodiment, in the biocompatible implant a linker is bound to said metal, metal alloy or metal oxide surface and to said antioxidant, ester of such compound, a pharmaceutically acceptable salt thereof or a combination thereof.

Whenever a linker is mentioned in the context of the present invention, this refers to a chemical entity that is used for binding said antioxidant, an ester, a pharmaceutically acceptable salt, or combination thereof, to the metal, metal alloy or metal oxide surface, of the biocompatible implant, thereby forming a covalent bond between the antioxidant and the linker and between said linker and the metal, metal alloy and/or metal oxide. Thus, one part of the linker reacts with, and thereby binds to, the metal, metal alloy or metal oxide surface.

Another part of the linker reacts with and binds to said antioxidant, thereby forming a covalent bond (or another type of chemical interactions such as electrostatic forces) between said antioxidant and said metal, metal alloy or metal oxide surface. This may provide for a surface of said biocompatible implant which is a particularly active modulator, preferably improver, of osseointegration and soft tissue attachment. Examples of linkers that may be used in the context of the present invention are linkers selected from the group consisting of anhydrides, alcohols, acids, amines, epoxies, isocyanates, silanes, thiol, alkyl, aryl, halogenated groups, and polymerizable groups.

In a preferred embodiment, the linker is a silane, and more preferably 3-aminopropyltriethoxysilane (APTES) or triethoxysilanepropylsuccinic acid (TESPSA).

In another preferred embodiment, the linker is a polyether and more preferably polyethilenglycol (PEG) or any of its derivatives. In the present invention, said PEG derivatives contain a PEG molecule base with a variety of reactive groups, functional groups or labels:
  with one group, with two groups (identical=homobifunctional; different: heterobifunctional) and more groups (multifunctional) being said groups for example, but not limited to, amine, carboxyl, aldehyde, thiol, hydroxyl, succinimyl, carbonyl imidazole, tossyl, nitrophenylcarbonate, maleimidyl, O-pyridyl disulfide, hydrazide, azide, alkyne, isocyanate, epoxide or silane.
  with labels or ligands such as, but not limited to, biotin, fluorescein or DSPE.

In another preferred embodiment, the metal(s), metal alloy(s) or metal oxide(s) of the implant is/are selected from the group consisting of titanium, an alloy or an oxide thereof, zirconium, an alloy or an oxide thereof, tantalum, an alloy or an oxide thereof, hafnium, an alloy or an oxide thereof, niobium, or an alloy or an oxide thereof, chromium-vanadium alloy and stainless steel. In a more preferred embodiment, the metal, metal alloy or metal oxide is titanium.

In the present invention, the phrase "implant" includes within its scope any device intended to be implanted into the body of a vertebrate animal, in particular a mammal, such as a human. Non-limiting examples of such devices are medical devices that replace anatomy or restore a function of the body such as the femoral hip joint; the femoral head; acetabuiar cup; vascular stents, elbow including stems, wedges, articular inserts; knee, including the femoral and tibial components, stem, wedges, articular inserts or patellar components; shoulders including stem and head; wrist; ankles; hand; fingers; toes; vertebrae; spinal discs; artificial joints; dental implants; ossiculoplastic implants; middle ear implants including incus, malleus, stages, incus-stapes, malleus-incus, malleus-incus-stapes; cochlear implants; orthopaedic fixation devices such as nails, screws, staples and plates; heart valves; pacemakers; catheters; vessels; space filling implants; implants for retention of hearing aids; implants for external fixation; prosthetic discs for spinal fixation and also intrauterine devices (IUDs), as well as bioelectronic devices such as intracochlear or intracranial electronic devices. Included are also surgical implants.

In a preferred embodiment, the implant of the present invention is selected from the group consisting of a surgical implant, an orthopedic implant, a dental implant, an orthopedic fixation device, an orthopedic joint replacement, a prosthetic disc for spinal fixation, or a graft material, preferably a metal oxide scaffold comprising titanium oxide.

In the present context, the term "orthopedic implant" includes within its scope any device intended to be implanted into the body of a vertebrate animal, in particular a mammal such as a human, for preservation and restoration of the function of the musculoskeletal system, particularly joints and bones, including the alleviation of pain in these structures. Within this context are also envisaged orthopedic fixation devices and orthopedic joint replacements.

In the present context, the term "dental implant" includes within its scope any device intended to be implanted into the oral cavity of a vertebrate animal, in particular a mammal such as a human, in tooth restoration procedures. Dental implants may also be denoted as dental prosthetic devices. Generally, a dental implant is composed of one or several implant parts. For instance, a dental implant usually comprises a dental fixture coupled to secondary implant parts, such as an abutment and/or a dental restoration such as a crown, bridge or denture. However, any device, such as a dental fixture, intended for implantation may alone be referred to as an implant even if other parts are to be connected thereto.

In the context of the present invention, the terms "implant", "medical implant", "graft material", "device" and "medical device" may be used interchangeably herein. It should be understood that in all aspects of the present invention, whenever a "biocompatible implant" or an "implant" is referred to herein this includes any of the implants mentioned herein and/or which is known to the skilled person to be suitable for the present purpose.

In another preferred embodiment, other biomolecules are present on a metal metal alloy or metal oxide surface of the implant, said biomolecules being selected from the group consisting of natural biomolecules, synthetic biomolecules, and recombinant biomolecules, such as bioadhesives, cell attachment factors, biopolymers, blood proteins, enzymes, extracellular matrix proteins and biomolecules, growth factors and hormones, nucleic acids (DNA and RNA), receptors, synthetic biomolecules, vitamins, drugs, biphosphonates, biologically active ions, fluoride, and marker biomolecules.

Another aspect of the present invention is related to a method for producing a biocompatible implant as previously described, comprising contacting and reacting an antioxidant compound as defined previously with the surface of said biocompatible implant.

In a preferred embodiment, said method comprises the steps of:
  a. chemically pre-treating the surface of an implant, and
  b. contacting and reacting an antioxidant compound as defined previously with said chemically pre-treated surface.

In a preferred embodiment, before step b), a step of contacting and reacting a linker as defined previously with said chemically pre-treated surface obtained in step a) is performed, and wherein in step b) antioxidant compound is reacted with said linker.

In another preferred embodiment, before step b), a step of contacting and reacting a linker as defined previously with said antioxidant compound is performed, and wherein in step b) antioxidant-linker conjugate is reacted with said pretreated surface obtained in step a).

In another preferred embodiment, the selected antioxidants are immobilized on the implant surface using procedures known by a skilled person, although these procedures may be selected from adsorption, covalent coupling, electrochemical surface modifications and self organized organic layers. In a more preferred embodiment, said immobilizing method of the antioxidant is covalent coupling.

In another preferred embodiment, after reacting the antioxidant compound with the linker, a reduction step is performed. This step can be carried out by any reduction agent known in the art although sodium cyanoborohydride ($NaCNBH_3$) is preferred.

In a preferred embodiment, the pretreatment step is selected from piranha attack, passivation, UV irradiation, acid or alkaline attack.

In another aspect, the present invention also relates to a method for introducing a biocompatible implant as defined herein into a patient in need thereof, said method comprising the steps of providing a biocompatible implant comprising one or more metal(s), metal alloy(s) and/or metal oxide(s), wherein to at least a part of a metal, metal alloy or metal oxide surface of said biocompatible implant a compound selected from the group consisting of flavonoid or methoxytriptophols, and/or a pharmaceutically acceptable salt thereof and/or a combination thereof is covalently bound and thereafter introducing said implant into said patient by a surgical procedure. An implant of the invention may be introduced into a patient who needs a replacement of a body part, such as a hip or a knee, and where modulation, preferably improvement, of osseointegration properties is needed.

The patient is preferably a mammal, and more preferably a human.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples and drawings are provided by way of illustration and are not intended to be limiting of the present invention.

EXAMPLES

Example 1

Immobilization of Flavonoids on Titanium Surfaces by Adsorption, Covalent Binding and Drop Casting Procedures

Figure 1:
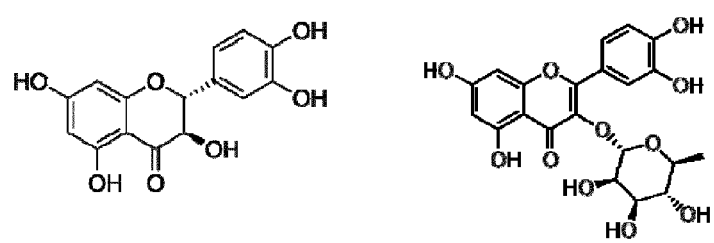
FIG. 1. Taxifolin (a) and quercitrin (b) molecular structures.

This example shows how flavonoids taxifolin and quercitrin (FIG. 1) can be immobilized on titanium surfaces by different methodologies.

Materials and Methods 1.1 Reagents and Materials.

Titanium disks, cp grade IV, polished or machined, had 6.25 mm diameter and 2 mm height. Technical acetone was purchased to Fisher Scientific. Nitric acid 69.5%, reagent grade, and absolute ethanol and anhydrous toluene were purchased to Scharlau. Deionized milliQ water was obtained from a Millipore system. Hellmanex III solution was purchased to Helima Hispania. (3-aminopropyl)triethoxysilane (APTES), taxifolin, quercitrin and NaCNBH$_3$ 5M in 1M NaOH were purchased from Sigma.

1.2 Titanium Cleaning and Surface Pretreatment

Polished or machined grade 4 Ti disks were cleaned according to the following steps: Immersion in deionized (DI) water for 30 s followed by 70% ethanol for 30 s. Then ultrasonication in DI water at 40° C., 5 min. Immersion in 40% NaOH, 40° C., 10 min. Again ultrasonication in DI water at 40° C., 5 min. Rinsed with DI water until pH=6. Ultrasonication in DI water, 50° C., 5 min. Immersion in 50% HNO$_3$, 50° C., 10 min. Again ultrasonication in DI water, 40° C., 5 min. Finally, Ti disks were rinsed with DI water until pH=6 and stored in 70% Ethanol.

Ti surfaces were hydroxilated before the flavonoid immobilization procedure according to one of the following methods: UV irradiation or passivation. UV irradiation: Ti surfaces were exposed to UV irradiation ($\lambda$=302 nm) for 48 h immediately before flavonoid immobilization. This ensures a high hydrophilicity (contact angle=0°) immediately after. Passivation: Passivation of titanium disks was performed following ASTM F86 standard: immersion in 3:7 (v/v) HNO$_3$-DI water solution, 30 min, RT. Rinsed with DI water and placed in a covered ultrapure water bath for 24 h. Implants were dried in a nitrogen stream immediately prior to the next functionalization step.

1.3 Immobilization by Adsorption

Pretreated Ti implants were immersed in a flavonoid solution in ethanol (taxifolin 400 µM or quercitrin 1000 µM) and stirred 24 h at 4° C. Then disks were rinsed with ethanol and dried with N$_2$.

1.4 Immobilization by Drop Casting

Pretreated Ti substrates were placed in a 96 well plate and 10 µl of flavonoid solution in absolute ethanol were drop casted on each implant surface. The implants were left to air dry for 30 min.

1.5 Covalent Immobilization

Figure 2:
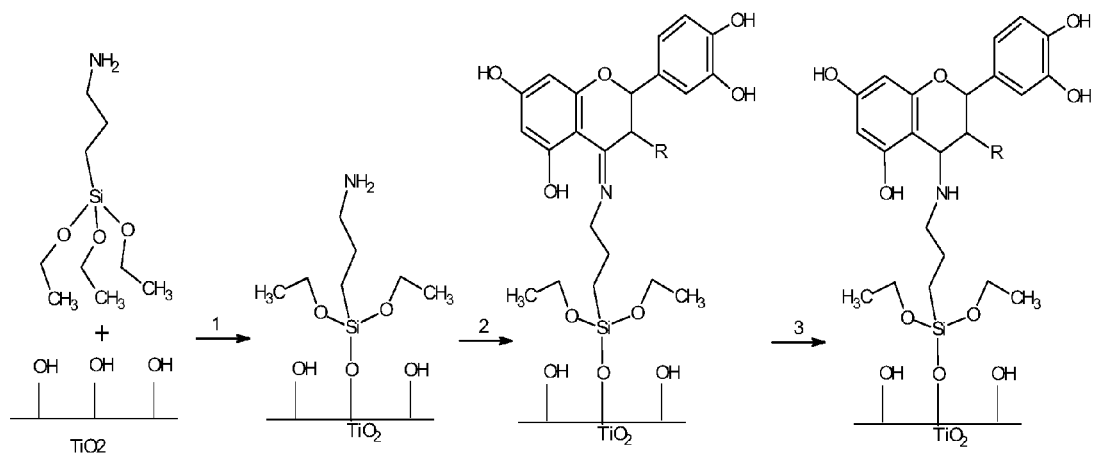
FIG. 2. (1) Reaction of the pretreated $Ti/TiO_2$ surface with (3-aminopropyl)triethoxysilane (APTES). (2) Reaction of the amine group of APTES with the carbonyl group of the flavonoid to form a Schiff base (—C=N—) and (3) reduction of the Schiff base with $NaCNBH_3$ to give a stable —C—NH-bond.

FIG. 2 shows the procedure for the covalent grafting of taxifolin and quercitrin on pretreated Ti/TiO$_2$ surfaces. Covalent immobilization was performed in two or three steps depending on the final product desired: Schiff base or reduced Schiff base. Schiff base formation (reversible C=N bond between APTES and flavonoid) was carried out in two steps: 1) Silanization of the substrate with APTES, 2) Biomolecule immobilization by reaction of the flavonoid carbonyl group with the amine group of the silane giving the Schiff base. Reduced Schiff bases (irreversible C-NH bond) were obtained adding a third step 3) Reduction with NaCNBH$_3$.

1) Silanization of TiO$_2$/Ti substrates with (3-aminopropyl) triethoxysilane (APTES): The silanization step was performed immediately after Ti pretreatment, in anhydric conditions, immersing the implants in a 2% v/v APTES solution in dry toluene for 24 h at room temperature. Then silanized disks were gently rinsed with toluene, acetone and ethanol and dried with N$_2$.

2) Taxifolin and Quercitrin immobilization (Schiff base formation): Silanized disks were immersed in 1 mM flavonoid solution in water at pH 5, stirred 1 h at RT, rinsed with DI water and dried with N$_2$.

3) Irreversible bond formation (Schiff base reduction): Immediately after the flavonoid linking step, disks were immersed in a solution of NaCNBH$_3$ 50 µM in DI water and stirred 1 h at RT, rinsed twice with DI water and dried with N$_2$.

1.6 Surface Physic-Chemical Characterization by Infrared Spectroscopy—Attenuated Total Reflectance (FTIR-ATR) Coupled to Optical Microscopy.

Samples were characterized using an FTIR-ATR spectrophotometer (Bruker Tensor 27) coupled to an UV-vis/IR microscope (Bruker Hyperion 3000). For each sample, a representative area of the implant surface was selected and at least 10 random measurement points were chosen. An FTIR spectrum was recorded for each point (resolution: 4 cm$^{-1}$, n° scans: 16, reference: air). Two sample replicates were measured. FTIR spectra of pure taxifolin and quercitrin were obtained from 50 mM stock solutions in ethanol using the ATR accessory (4 µl of the biomolecule solution were deposited on the ATR crystal and the measurement was done after solvent evaporation).

1.7 Biomolecule Release by UV-vis Spectrometry

The biomolecule release from functionalized implants after 24 h incubation in water at pH 7.5 and 37° C. was determined by UV-Vis spectroscopy. Implants were placed in a 96 well plate and 200 µl of water at pH 7.5 were added to each well. Samples were incubated at 37° C. during 24 h. Then, a 150 µl aliquot was withdrawn and the absorbance ($\lambda_{max}$ taxifolin=290 nm, $\lambda_{max}$ quercitrin=350 nm) was measured using a Biotek UV-vis plate reader spectrophotometer. Two sample replicates were measured.

Results 1.11 Results for Adsorption Technique

Table 1 shows the experiments carried out for immobilizing taxifolin and quercitrin by adsorption on Ti polished disks, either passivated (FL1) or UV treated (FL2). To check the presence of the flavonoids on the substrates, the amount of biomolecule released in water at pH 7.5—to simulate physiologic conditions—was determined by UV-Vis spectroscopy after 24 h incubation at 37° C.

TABLE 1

Adsorption experiments carried out for the functionalization of Ti substrates with taxifolin (TX) and quercitrin (QR) and biomolecule released to water media at pH 7.5, after 24 h incubation at 37° C. C is the concentration of flavonoid released to 200 µl of water media.

| Imm. Method | Experiment | Ti pretreat. | Biomolecule | C µM, 24 h |
|---|---|---|---|---|
| Adsorption | FL1 | Passivation | FL1 TX | 20.88 ± 3.30 |
| | | | FL1 QR | 39.23 ± 13.51 |
| | FL2 | UV | FL2 TX | 21.87 ± 7.53 |
| | | | FL2 QR | 30.69 ± 3.28 |

TABLE 1-continued

Adsorption experiments carried out for the functionalization of Ti substrates with taxifolin (TX) and quercitrin (QR) and biomolecule released to water media at pH 7.5, after 24 h incubation at 37° C. C is the concentration of flavonoid released to 200 μl of water media.

| Imm. Method | Experiment | Ti pretreat. | Biomolecule | C μM, 24 h |
|---|---|---|---|---|

In all cases either taxifolin or quercitrin was detected in the aqueous media after 24 h incubation. The released amount of quercitrin was slightly higher than taxifolin in both experiments FL1 and FL2, maybe due to the higher initial concentration of quercitrin used (1 mM quercitrin, 400 μM taxifolin). Comparing Ti pretreatments, the amount of flavonoid released from adsorption samples is similar for Ti pretreatments, passivation and UV irradiation.

1.12 Results for Drop Casting Technique

Table 2 shows the experiments carried out for immobilizing taxifolin and quercitrin by drop casting. Machined Ti was used for these experiments since this method was also used to test the in vitro effect of the implants (Examples 2 and 3) and machined surfaces are preferred for in vitro studies. Passivation was used as Ti pretreatment.

Figure 3A:
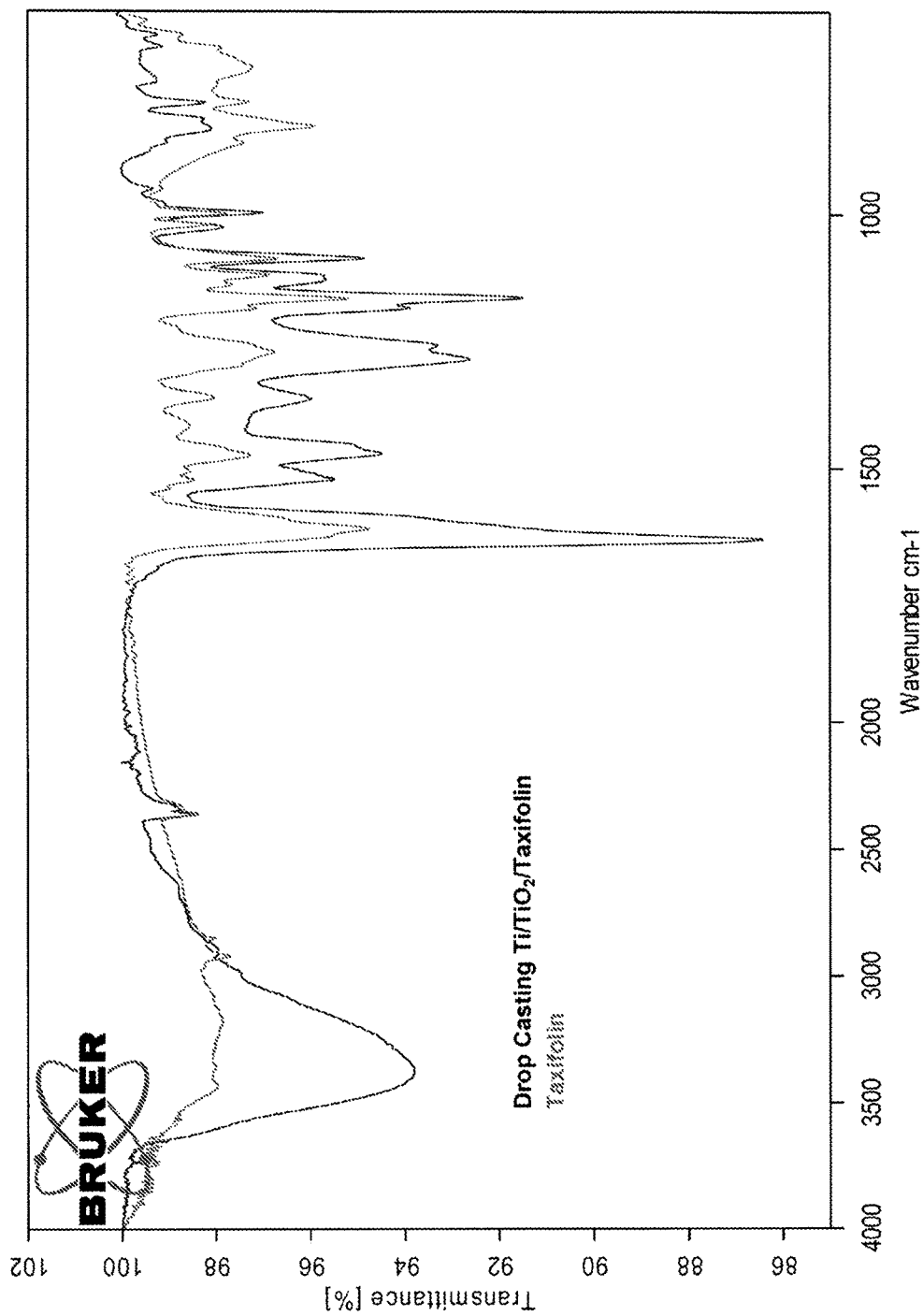
FIGS. 3A and 3B. Comparison of FTIR-ATR average spectra of $Ti/TiO_2$ samples coated by drop casting with a) taxifolin (FIG. 3A) and b) quercitrin (FIG. 3B), with the spectrum of the pure compound. Each spectrum corresponds to the average of at least ten measurement points along the implant surface.
Figure 3B:
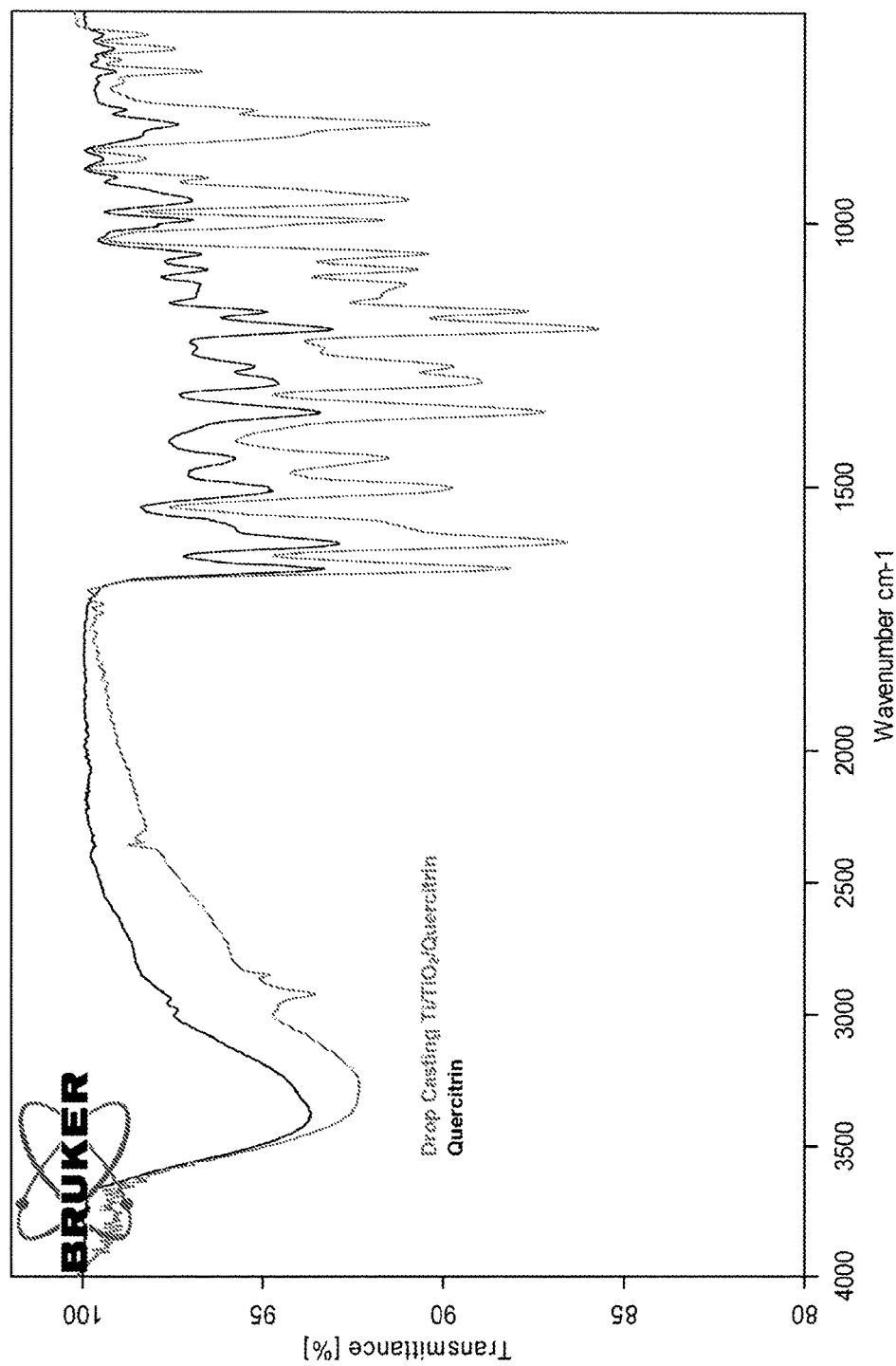

FIGS. 3A and 3B show the FTIR spectra obtained on different measurement points of drop casted implants. Comparing the spectra obtained with that of the pure flavonoid it is clearly shown that either taxifolin or quercitrin were homogeneously detected on drop casted Ti surfaces. Table 2 also shows the amount of biomolecule released from the implant surface to water media after 24 h incubation at 37° C., measured by UV-Vis spectroscopy. The maximum biomolecule release expected for experiment FL13 were 30 μM taxifolin and 500 μM quercitrin, and for experiment FL16 100 μM taxifolin and 250 μM quercitrin. As the Table shows, in all cases taxifolin or quercitrin were clearly detected in the media after the 24 h incubation.

TABLE 2

Drop Casting experiments carried out for the functionalization of Ti substrates with taxifolin (TX) and quercitrin (QR) and biomolecule released water media at pH 7.5, after 24 h ncubation at 37° C. C is the concentration of flavonoid released to 200 μl of water media. Expected C max is the expected concentration of biomolecule assuming that the entire amount of flavonoid initially added is released in these conditions.

| Imm. Method | Experiment | Biomolecule | C μM, 24 h | Expected $C_{max}$ μM |
|---|---|---|---|---|
| Drop Casting | FL13 | FL13 TX | 28.5 ± 1.8 | 30 |
| | | FL13 QR | 408.3 ± 18.4 | 500 |
| | FL16 | FL16 TX | 98.8 ± 3.3 | 100 |
| | | FL16 QR | 167.6 ± 13.2 | 250 |

1.13. Results for Covalent Immobilization Technique

Table 3 shows the evaluated groups to covalently immobilize taxifolin and quercitrin on Ti subtrates. Ti substrates were either UV irradiated or passivated. For each pretreatment, Schiff base formation and Schiff base reduction were evaluated. Samples were characterized by FTIR-ATR spectroscopy to check the presence of the flavonoid on the surface. Biomolecule release after 24 h incubation in water at pH 7.5 and 37° C. was also determined.

TABLE 3

Covalent functionalization of Ti substrates with taxifolin (TX) and quercitrin (QR) through an APTES coupling agent. The table shows the Ti pretreatment (UV irradiation or passivation), the reduction or not of the Schiff base obtained, the biomolecule used and the release (C μM) of flavonoid to water media after 24 h of incubation in water at pH 7.5 and 37° C.

| Imm. Method | Ti Pretreat. | Reduction step | Biomolecule | C μM, 24 h |
|---|---|---|---|---|
| Covalent linking | | No | TX | 5.06 ± 0.59 |
| | | | QR | 3.33 ± 0.10 |
| | UV | Yes | TX | No det. |
| | | | QR | No det. |
| | Passiv | No | TX | 10.22 ± 1.88 |
| | | | QR | 8.54 ± 0.41 |
| | | Yes | TX | No det. |
| | | | QR | No det. |

Figure 4A:
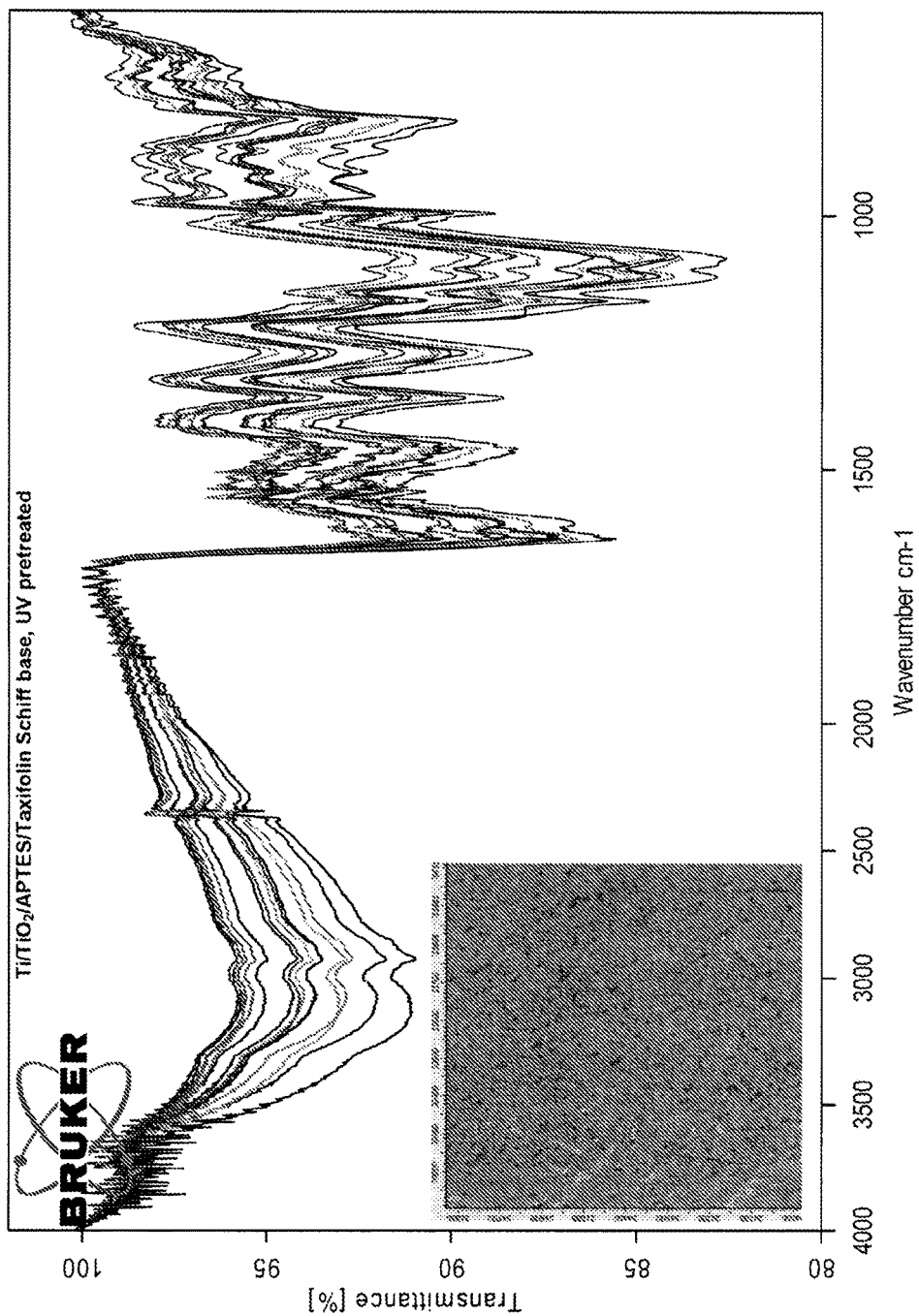
FIGS. 4A and 4B. FTIR of flavonoids covalently grafted to UV irradiated Ti surfaces. a) in FIG. 4A, FTIR-ATR spectra of a surface coated with taxifolin by Schiff base formation, UV pretreated. Each spectrum corresponds to one measurement point on the implant surface. Measurements points are marked in the insert image. Bands correspond to taxifolin. A band at 2900 $cm^{-1}$ can be assigned to aliphatic $CH_2$ stretching indicating the presence of the APTES crosslinker. b) in FIG. 4B, Comparison of FTIR spectra obtained in non reduced and FL6 reduced quercitrin Schiff base surfaces. Each spectra corresponds to the average of 10 measurement points along the surface.
Figure 4B:
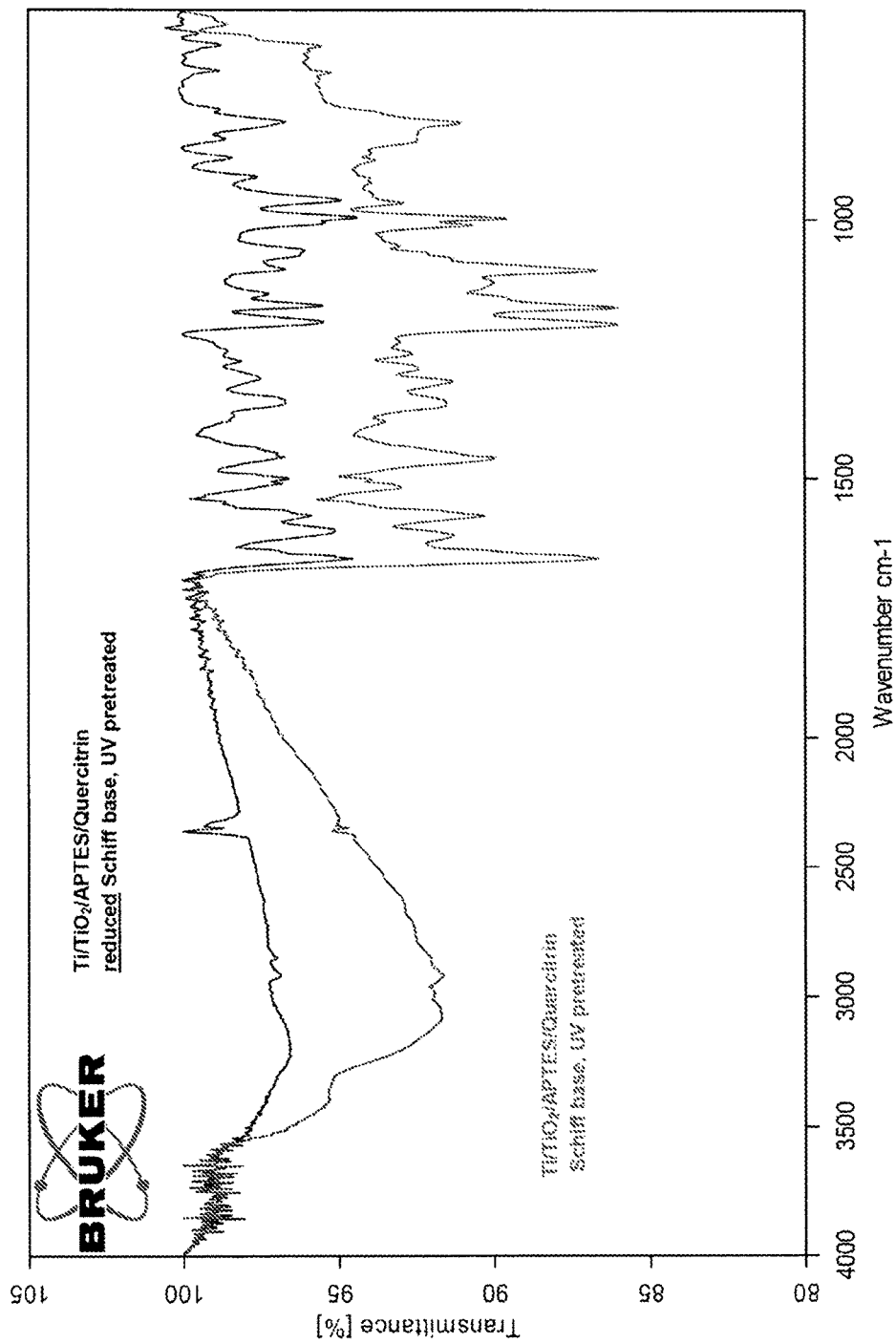
Figure 5A:
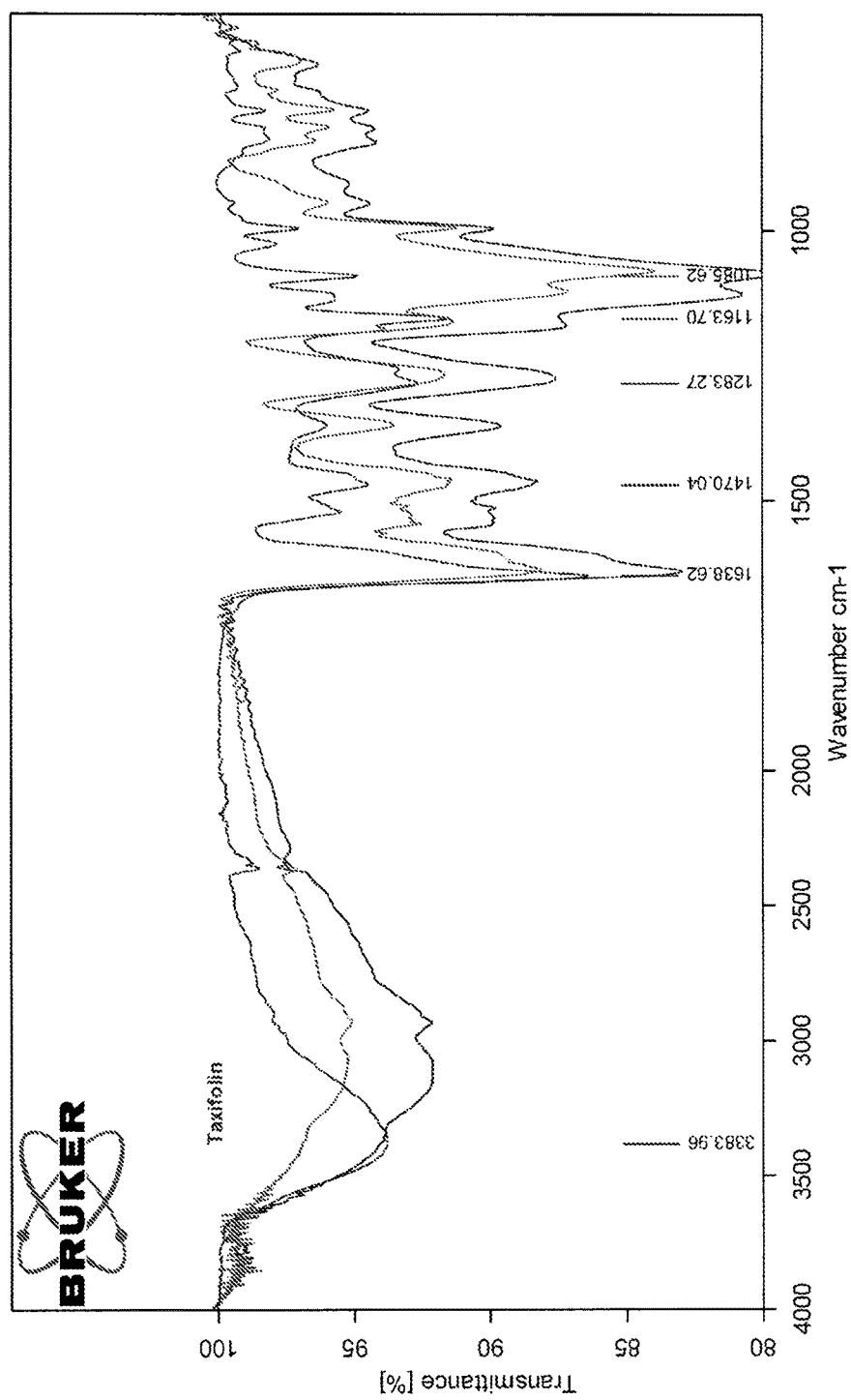
FIGS. 5A and 5B. FTIR of taxifolin covalently grafted to passivated Ti surfaces a) in FIG. 5A, FTIR-ATR spectra of Schiff base surfaces compared to the spectra of pure taxifolin. Each spectra corresponds to the average of ten. B) in FIG. 5B, Comparison of FTIR spectra of reduced Ti/TiO2/APTES/Taxifolin surface with pure taxifolin.
Figure 5B:
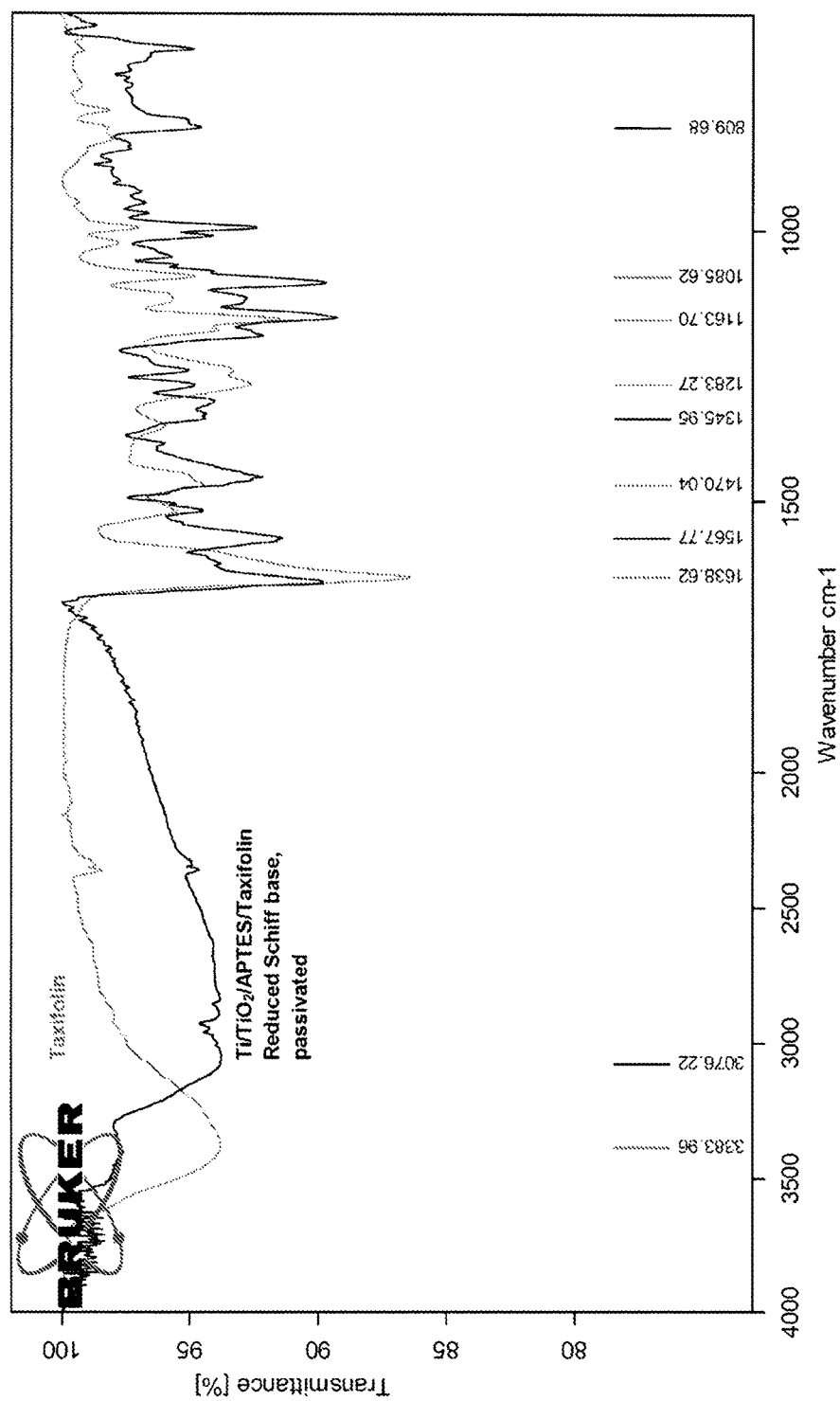
Figure 6:
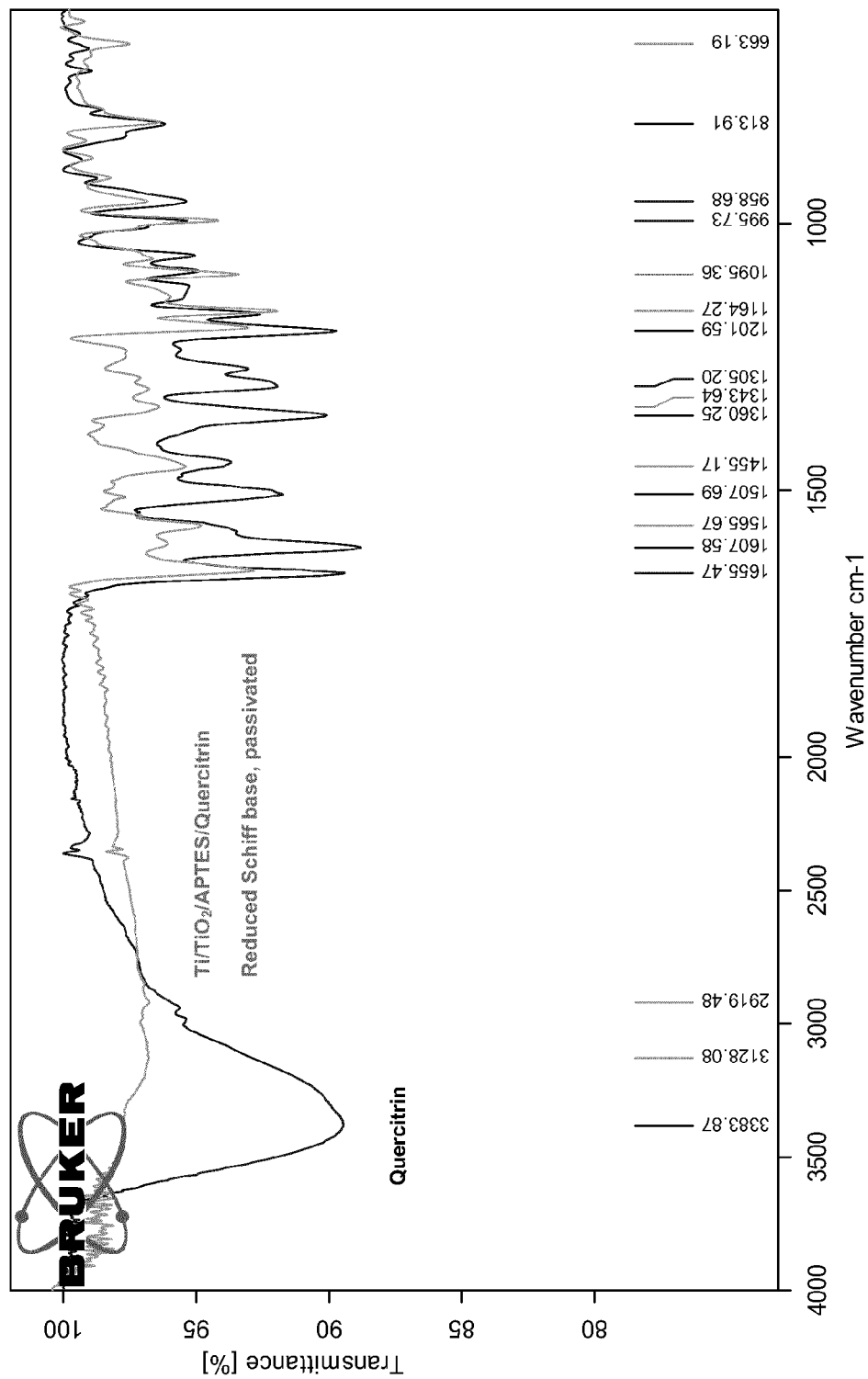
FIG. 6. Comparison of FTIR spectra of reduced Ti/TiO2/APTES/Quercitrin surface obtained on passivated substrates and pure quercitrin.

Flavonoids were homogenously detected by FTIR-ATR for all the groups studied. FIGS. 4A and 4B show some representative FTIR spectra obtained on functionalized UV pretreated samples. Each spectrum of FIG. 4A corresponds to one measurement point of a taxifolin coated sample. The spectra bands corresponded clearly to taxifolin. A band at 2900 cm$^{-1}$ can be assigned to $CH_2$ stretching and the broad bands at 1119-1009 cm$^{-1}$ to Si-O-R vibrations, indicating also the presence of the APTES crosslinker. FIG. 4B shows the presence of quercitrin grafted to UV pretreated surfaces, before and after the reduction step. FIGS. 5A, 5B and 6 show representative FTIR-ATR spectra of taxifolin and quercitrin covalently grafted to passivated samples. The presence of $CH_2$ bands at 2900 cm−1 in all the FTIR spectra of the functionalized samples also indicates the presence of APTES on the surface.

Table 3 also shows the amount of flavonoid released after 24 h at 37° C. from covalently bound samples, measured by UV-vis spectroscopy. As the table shows, in all Schiff base formation experiments without reduction step, taxifolin or quercitrin were detected in the water media, in low concentrations. The flavonoid detected could correspond to some crystal aggregates observed by SEM, being probably flavonoid residues of the rinsing step. However, since Schiff bases have weak bonds that rapidly hydrolyze (reverse), some part of the detected concentration could also correspond to the hydrolysis of the Schiff base. By the other hand, the concentration of flavonoid released to water media from reduced Schiff base samples was no detectable. This agrees with the expected formation of an irreversible bond between the flavonoid and the silanized surface when reducing the Schiff base with $NaCNBH_3$.

Conclusions Example 1

Flavonoids taxifolin and quercitrin can be grafted to Ti surfaces either by adsorption, drop casting and covalent linking methods. UV irradiation and passivation are effective pretreatments for Ti surface activation before the immobilization of the biomolecule.

Flavonoid-coated samples by adsorption and drop casting showed a high release of the flavonoid from the surface after 24 h incubation in water at physiological conditions.

Covalently grafted samples showed different release behaviors depending on the reduction step. Non-reduced samples showed a low release of the flavonoid from the surface in water after 24 h incubation, while reduced samples using the same conditions did not show release of the flavonoid. As FTIR-ATR analysis of covalently immobilized samples showed the presence of the flavonoids on the Ti surface both for non-reduced and reduced samples, this demonstrates that the flavonoids are covalently linked to the substrate through the APTES silane crosslinker.

Example 2

Titanium Surfaces Functionalized with Flavonoids: Biocompatibility and Bioactivity on Human Gingival Fibroblasts Machined titanium surfaces were functionalized by three methodologies: drop casting, covalent linking by Schiff base formation and covalent linking by reduced Schiff base, as described in Example 1. Surface chemical analysis was carried out by FTIR-ATR spectroscopy. Flavonoid release profiles up to 14 days from the different surfaces were determined by UV-Vis spectroscopy. The biocompatibility and bioactivity of the different flavonoid-coated titanium surfaces were assessed in cell culture models of human gingival fibroblasts (HGF), as a cell model for soft tissue around titanium implants. Fibroblasts cultured on flavonoid modified titanium surfaces were tested for cell toxicity, determined by lactate dehydrogenase (LDH) activity after 24 hours of incubation, cell morphology, determined by SEM and cytoskeleton and nuclei staining, and gene expression of differentiation markers after 14 days of culture.

Table 4 shows the different surfaces produced. Prior to biomolecule immobilization, passivation of machined titanium disks was carried out for all groups.

TABLE 4

Groups used in the study.

| Group | Modification |
|---|---|
| FL13B | Passivated, Ti/TiO$_2$ |
| FL13TX | Drop casting, Ti/TiO$_2$/Taxifolin |
| FL13QR | Drop Casting, Ti/TiO$_2$/Quercitrin |
| FL14A | Silanized Ti, Ti/TiO$_2$/APTES |
| FL14TX | Schiff base, Ti/TiO$_2$/APTES/Taxifolin |
| FL14QR | Schiff base, Ti/TiO$_2$/APTES/Quercitrin |
| FL15TX | Reduced Schiff base, Ti/TiO$_2$/APTES/Taxifolin |
| FL15QR | Reduced Schiff base, Ti/TiO$_2$/APTES/Quercitrin |

2.1. Flavonoid Release Profile by UV-Vis Spectroscopy

The flavonoid release profile from coated surfaces in water media, simulating physiologic conditions (pH 7.5, 37° C.) was measured by UV-Vis spectroscopy. Implants were placed in a 96 well plate and 200 µl of water at pH 7.5 were added to each well. Aqueous media (200 µl/sample) was changed at time 1 h, 1 day and 4, 6, 8, 11 days, simulating culture media changes. Each time, a 150 µl aliquot was withdrawn and the absorbance ($\lambda_{Taxifolin}$=290 nm, $\lambda_{Quercitrin}$=350 nm) was measured in a 96 well Elisa plate using a Biotek UV-vis plate reader spectrophotometer. The concentration of flavonoid was calculated from interpolation of data in flavonoid standard calibration curves. Two replicates were measured for each sample. Passivated Ti substrates were used as blank samples for drop casted implants. Silanized Ti substrates were used as blank for covalently linked samples.

2.2. Cell Culture

Human gingival fibroblasts (HGF) were obtained from Provitro GmbH (Berlin, Germany). HGF cells were routinely cultured at 37° C. in a humidified atmosphere of 5% CO2, and maintained in fibroblast growth medium supplemented with 10% fetal calf serum (FCS) and antibiotics (50 ng amphotericin/ml and 50 µg gentamicin/ml) (Provitro GmbH, Berlin, Germany). Cells were subcultured 1:4 before reaching confluence using PBS and trypsin/EDTA, as recommended by suppliers. Experiments were performed with HGF cells at passage 7.

Titanium coin-shaped implants were placed in 96-well plates and HGF were seeded at a density of $1.0 \times 10^4$ cells/well for all control and test samples. Trypan blue stain was used to determine total and viable cell number. Culture media was refreshed every other day. Culture media was collected after 24 hours to test LDH activity. Some samples were processed by scanning electron microscopy and confocal microscopy. Cells were harvested after 14 days to study gene expression.

2.3. Determination of Cytotoxicity The presence of LDH activity in the culture media after 48 hours of incubation was used as an index of cell death. LDH activity was determined spectrophotometrically after 30 min of incubation at 25° C. of 50 µl of culture media and 50 µl of the reaction mixture, by measuring the oxidation of NADH at 490 nm in the presence of pyruvate, according to the manufacturer's kit instructions (Cytotoxicity Detection kit, Roche Diagnostics). Results from all the samples were presented relative to the LDH activity in the medium of cells treated with the vehicle control for each case, 1% ethanol or 0.6% DMSO, (low control, 0% of cell death) and of cells treated with 1% Triton X-100 (high control, 100% cell death). The percentage of LDH activity was calculated using the following equation: Cytotoxicity (%)=(exp.value−low control)/(high control−low control)*100.

2.4. Microscopic Analysis of Cells Grown on the Modified Ti Surfaces

A scanning electron microscope (SEM) using Back Scattered Electrons (BSE), 40 Pa of pressure and 10 kV of voltage was used to acquire images of cells grown on coin-shaped implants. Cells were washed twice with PBS and fixed with glutaraldehyde 4% in PBS for 1 hour. The fixative solution was removed, and the cells were washed with distilled water twice. At 30 minute intervals, the cells were dehydrated by the addition of 50%, 70%, 90% and 100% ethanol solutions. Finally, the ethanol was removed, and the cells were left at room temperature to evaporate the remaining ethanol prior to analysis.

Then, the samples were rehydrated by the addition of 90%, 70% and 50% ethanol solutions and water for 5 minutes periods. Cells were stained with Phalloidin-FITC 5 µg/ml (Sigma, St. Louis, Mo., USA) in PBS Triton X-100 0.2% for 30 minutes in the dark. Cells were washed with PBS and coin-shaped implants were placed on slides. Finally, a drop of Fluoroshield TM with DAPI (Sigma, St. Louis, Mo., USA) was added and cover glasses were mounted on the implants. Two implants of each group were used to perform the experiment and three images of each implant were taken with the confocal microscope (Leica DMI 4000B equipped with Leica TCS SPE laser system). Excitation wavelengths of DAPI and Phalloidin-FITC were set at 405 and 488 nm respectively; fluorescence was captured between 430-480 nm for DAPI and between 500-525 nm for Phalloidin-FITC.

2.5. RNA Isolation and Real-Time RT-PCR Analysis Total RNA was isolated using Tripure® (Roche Diagnostics, Mannheim, Germany), according to the manufacturer's protocol. Total RNA was quantified at 260 nm using a Nanodrop spectrophotometer (NanoDrop Technologies, Wilmington, Del., USA). The same amount of RNA (0.2 µg) was reverse transcribed to cDNA at 42° C. for 60 min using High Capacity RNA-to-cDNA kit (Applied Biosystems, Foster City, Calif.), according to the protocol of the supplier.

Aliquots of each cDNA were frozen (−20° C.) until the PCR reactions were carried out. Real-time PCR was performed for two reference genes, glyceraldehyde-3-phosphate dehydrogenase (GAPDH) and beta-actin (B-actin), and target genes (Table 5). Target genes genes are covering different aspects of gingival fibroblast function like ECM production and organization, and inflammation as detailed in the following table.

TABLE 5

Function of selected genes.

| Gene | Function |
| --- | --- |
| Collagen III α1 (COL3A1) | The gingival connective tissue consists of a dense network of collagen fibrils bundles that provide firmness to the gingiva and attach the gingiva to the tooth and alveolar bone. They also regulate functions of the connective tissue cells. COL3A1 is found in extensible connective tissues such as skin, lung, and the vascular system, frequently in association with type I collagen. |
| Interleukin-6 (IL6) | IL-6 is known to mediate important signals in the inflammatory cytokine network. Gingival fibroblasts secrete cytokines upon stimulation with inflammatory mediators, including IL-6. |

Real-time PCR was performed in the Lightcycler 480® (Roche Diagnostics, Mannheim, Germany) using SYBR green detection. Each reaction contained 7 µl Lightcycler-FastStart DNA MasterPLUS SYBR Green I (containing Fast Start Taq polymerase, reaction buffer, dNTPs mix, SYBR-Green I dye and MgCl2), 0.5 µM of each, the sense and the antisense specific primers (Table 6) and 3 µl of the cDNA dilution in a final volume of 10 µl. The amplification program consisted of a pre-incubation step for denaturation of the template cDNA (5 min 95° C.), followed by 45 cycles consisting of a denaturation step (10 s 95° C.), an annealing step (10 s 60° C.) and an extension step (10 s 72° C.). After each cycle, fluorescence was measured at 72° C. A negative control without cDNA template was run in each assay.

analysis on the LightCycler and subsequently 2% agarose/TAE gel electrophoresis to confirm amplification specificity, Tm and amplicon size, respectively. All samples were normalized by the geometric mean of the expression levels of ACTBL2 and GAPDH and fold changes were related to the control groups using the following mathematical model: ratio=$E_{target}^{\Delta Cp\ target\ (mean\ control-sample)}/E_{reference}^{\Delta Cp\ target\ (mean\ control-sample)}$, where Cp is the is the crossing point of the reaction amplification curve as determined by the LightCycler 480 software. Stability of reference genes was calculated using the BestKeeper tool.

All in vitro data are presented as mean values±SEM (standard error of the mean). The Kolmogorov-Smirnov test was done to assume parametric or non-parametric distributions for the normality tests. Differences between groups were assessed by Mann-Whitney-test or by Student t-test depending on their normal distribution. SPSS® program for Windows, version 17.0 (SPSS, Chicago, Ill., USA) was used. Results were considered statistically significant at p-values ≤0.05.

Results 2.6. Chemical Analysis of Flavonoid Coated Substrates by FTIR-ATR

The presence of flavonoids on the different surfaces was detected as shown in example 1.

2.7. Flavonoid Release Profile by UV-Vis Spectroscopy

Figure 7:
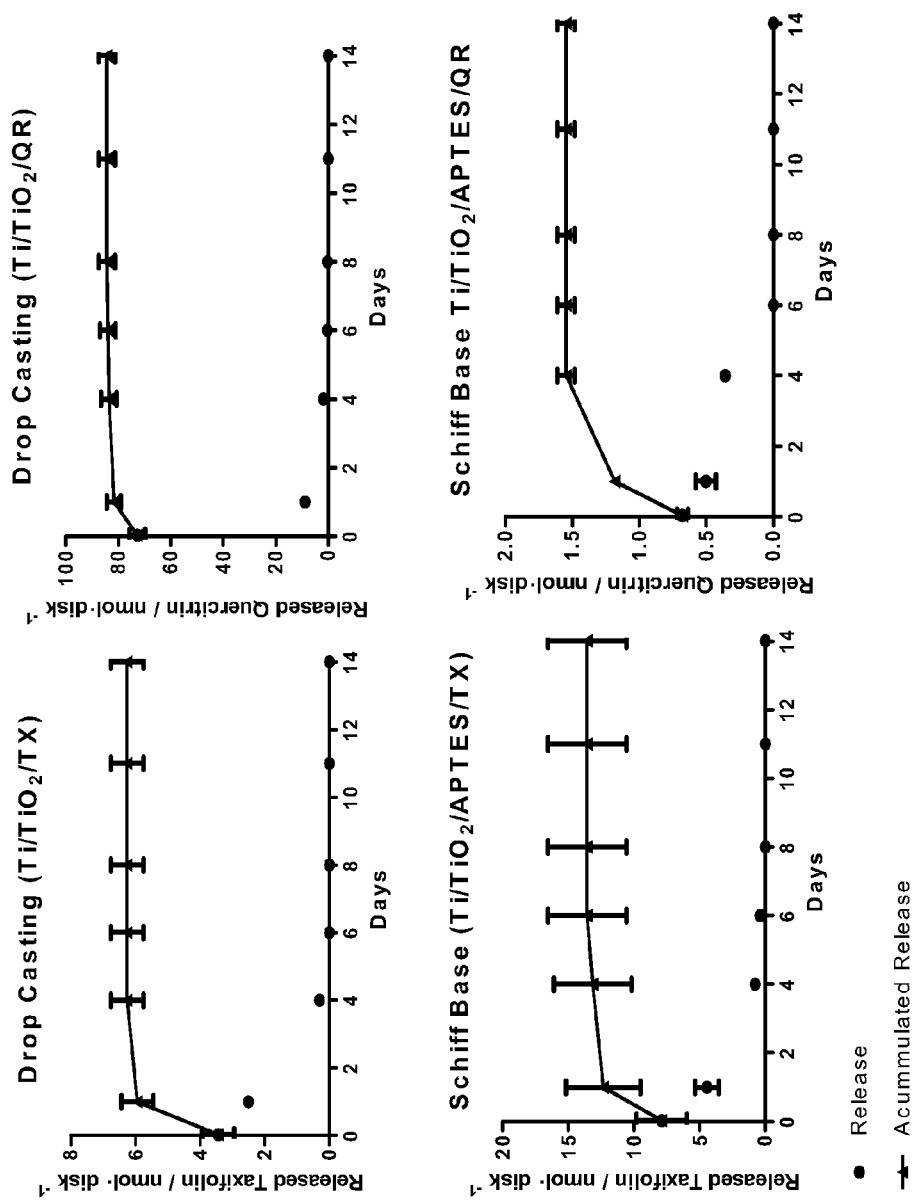
FIG. 7. Flavonoid release profile in aqueous media (pH 7.5, 37° C.) from samples coated by drop casting (top) and covalently linked by Schiff base formation (bottom), simulating HGF culture media changes. Left: taxifolin coated substrates, right: quercitrin coated.

FIG. 7 shows the flavonoid release profile in aqueous media up to 14 days, simulating physiologic conditions (pH 7.5, 37° C.), from drop casted (experiment FL13) and covalently linked by Schiff base formation (experiment FL14) samples.

Drop Casted substrates. The initial flavonoid amount deposited on the Ti surface by drop casting was 6 nmol/disk for taxifolin implants and 100 nmol/disk for quercitrin. Taxifolin release profile shows that almost 3.2±0.4 nmol were released to the media after 1 h of incubation and the release was almost complete at day 1. Quercitrin release profile from drop casted implants showed an initial burst at

TABLE 6

Primers used in the real-time PCR of reference and target genes. S: sense, A: antisense, bp: base pairs

| Gene | Primer sequence | Product size | GeneBank Accession Nr. |
| --- | --- | --- | --- |
| CollagenIII α1 (COL3A1) (target gene) | S: GGCCTACTGGGCCTGGTGGT<br>A: CCACGTTCACCAGGGGCACC | 190 bp | NM_000090.3 |
| Interleukin-6 (IL6) (target gene) | S: AGGAGACTTGCCTGGTGAAA<br>A: GCATTTGTGGTTGGGTCAG | 196 bp | NM_000600.3 |
| β-Actin (reference gene) | S: CTGGAACGGTGAAGGTGACA<br>A: AAGGGACTTCCTGTAACAATGCA | 136 bp | NM_001101.3 |
| GAPDH (ref. gene) | S: TGCACCACCAACTGCTTAGC<br>A: GGCATGGACTGTGGTCATGAG | 87 bp | NM_002046.3 |

Real-time efficiencies (E) were calculated from the given slopes in the

LightCycler 480 software using serial dilutions, showing all the investigated transcripts high real-time PCR efficiency rates, and high linearity when different concentrations were used. PCR products were subjected to a melting curve 1 h of 72.8±4.1 nmol. After 1 day of incubation, a 81.7% of the initially added amount (100 nmol/disk) was released to the media. From day 4 to day 14, the amount of quercitrin released to media was not detectable.

Covalently linked subtrates. FIG. 7 also shows the release profile of Ti surfaces functionalized with taxifolin and quercitrin by Schiff base formation (experiment FL14). In this experiment the Schiff bases obtained were not reduced. Therefore the C=N bond supposedly formed between the $NH_2$ terminated surface and the carbonyl group of the flavonoid should be reversible, and the flavonoid might be released from the substrate. Taxifolin release profile of Schiff base samples shows that 7.9±2.7 nmol of flavonoid were released to the media after 1 h of incubation. At day one the cumulative release was 12.4±4.0 nmol. From 1 to 14 days the released amount was not significant. A high deviation between replicates was observed. These differences between samples may be due to the reversible nature of the Schiff base formed or to different effectivity of the rinsing step after the immobilization. Quercitrin release from Schiff base samples was significantly lower than taxifolin. The total amount of quercitrin released after 14 days was 1.54±0.09 nmol. No taxifolin neither quercitrin were detected in the media from reduced Schiff base surfaces (experiment FL15). This agrees with the expected formation of an irreversible stable bond between the flavonoid and the APTES/Ti surface.

2.8. Biocompatibility of Flavonoid-Coated Titanium Surfaces with Human Gingival Fibroblasts.

Figure 8:
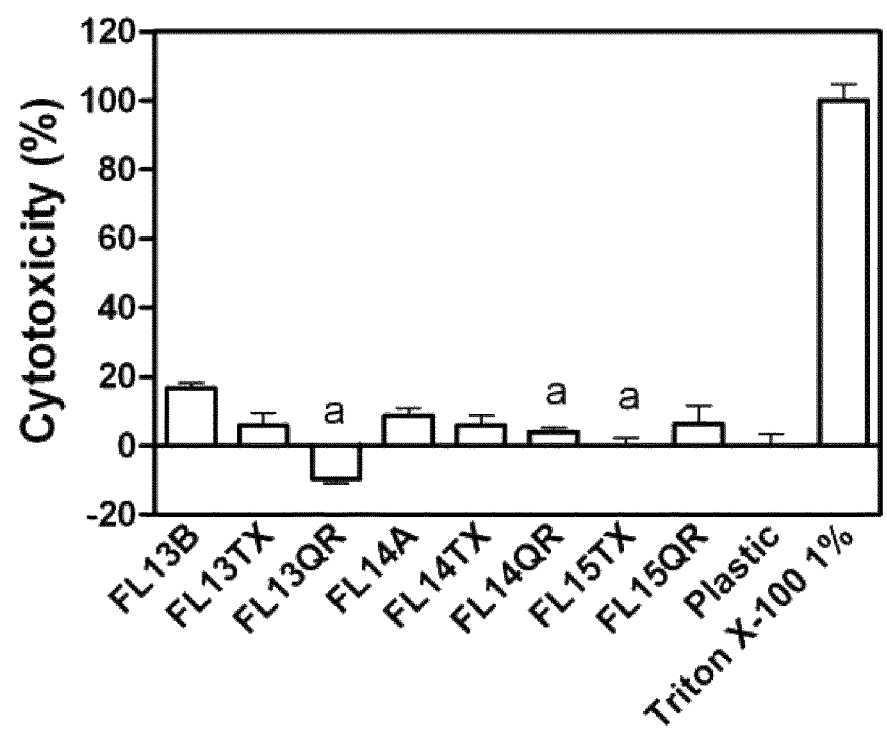
FIG. 8. LDH activity measured in culture media collected after 48 hours of treatment in human gingival fibroblasts. High control (100% cytotoxicity) was cell culture media from cells treated with 1% Triton X-100. Low control (0% cytotoxicity) was cell culture media from control vehicle cells. The percentage of LDH activity was calculated using the following equation: Cytotoxicity (%)=(exp.value–low control)/(high control–low control)*100. Values represent the mean±SEM (N=8). Differences between groups were assessed by Student t-test: *a<0.05 versus control (FL13B for FL13 groups; FL14A for FL14 and FL15 groups).

Cytotoxicity of treatments was evaluated by measuring the release of LDH from HGF to the culture media after 24 hours of treatment (FIG. 8). None of the surfaces were toxic for HGF. When comparing the flavonoid-coated groups with its controls, quercitrin drop casted surfaces (FL13QR) were significantly less cytotoxic than the passivated Ti control without flavonoid (FL13B) and covalently linked FL14QR and FL15TX were significantly less cytotoxic than the silanized Ti control without flavonoid (FL14A).

2.9. Effect of the Different Flavonoid-Coated Titanium Surfaces on Cell Morphology.

Figure 9:
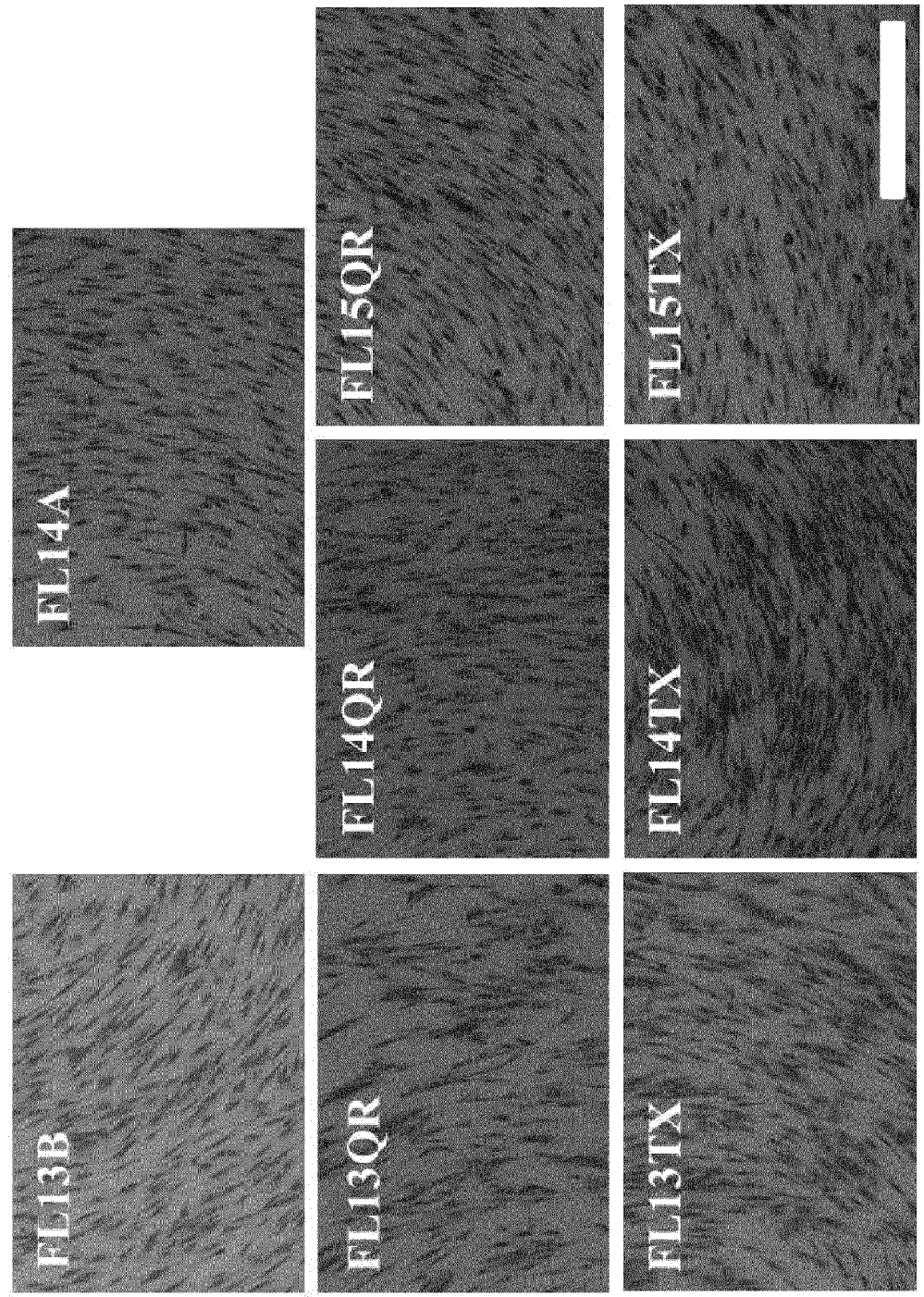
FIG. 9. Scanning electron microscope micrographs of human gingival fibroblasts on the different surfaces. Scale bar=500 μm.
Figure 10:
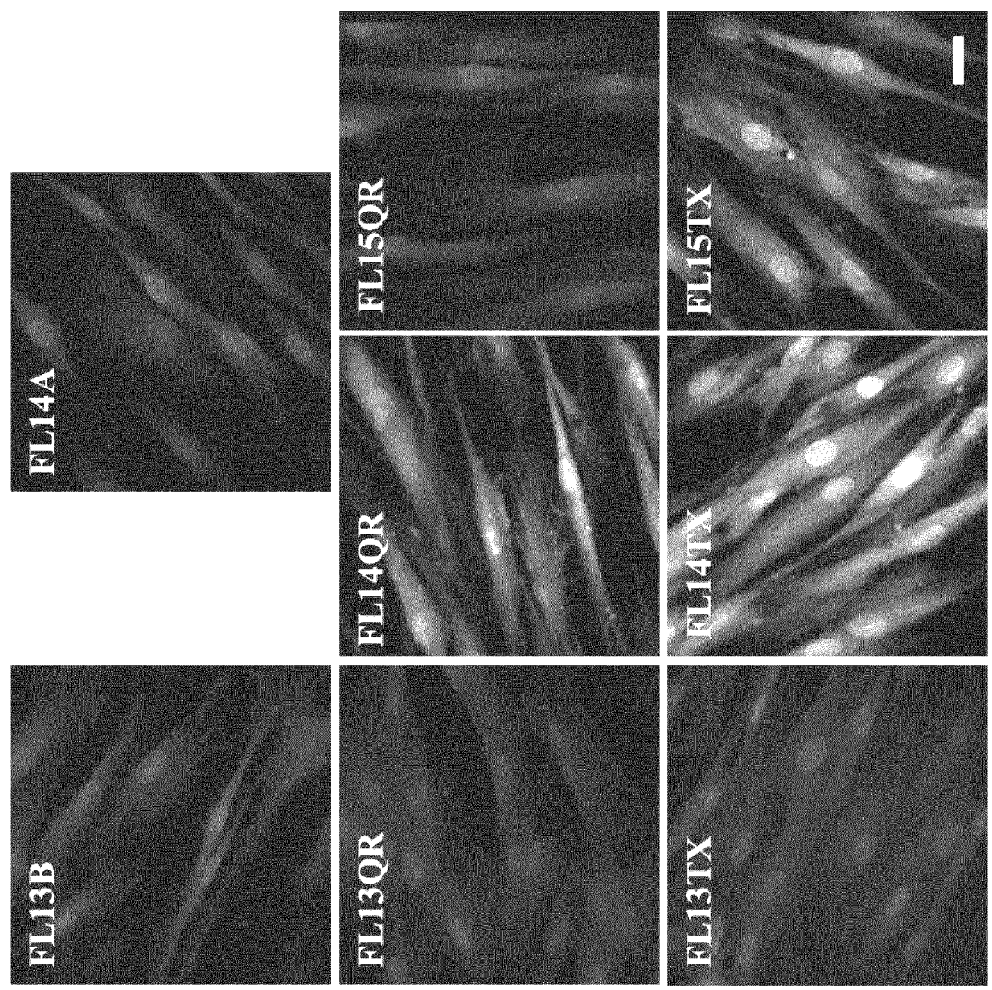
FIG. 10. Cytoskeleton and nuclei immunostaining of human gingival fibroblasts on the different surfaces. Scale bar=25 μm.

After 24 hours of culture on the different surfaces, HGF possessed the typical fibroblastic spindle-shaped morphology and were distributed throughout the entire surface (FIG. 9). Cytoskeleton and nuclei staining also revealed good cell spreading on all surfaces and the formation of prolongations and filopodia to contact each other and to attach to surfaces (FIG. 10). It is worth noting that HGF aligned to the concentric nanogrooves of the titanium surfaces. No differences on cell morphology were observed among the groups.

2.10. Effect of the Different Flavonoids on Gene Expression.

Figure 11:
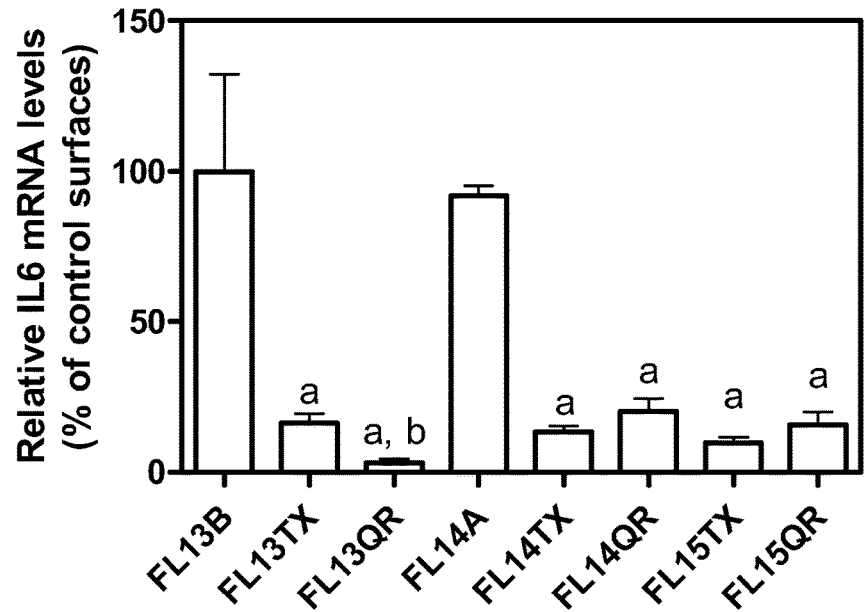
FIG. 11. Effect of the different surfaces on mRNA expression levels of IL6 in human gingival fibroblasts cultured for 14 days. Data were normalized to reference genes (beta-actin and GAPDH), expressed as percentage of control which was set to 100% (FL13B for FL13 groups; FL14A for FL14 and FL15 groups). Values represent the mean±SEM (N=6). Differences between groups were assessed by Student t-test: (a) p<0.05 versus control (FL13B for FL13 groups; FL14A for FL14 and FL15 groups); (b) p<0.05 differences between flavonoids in the same group.
Figure 12:
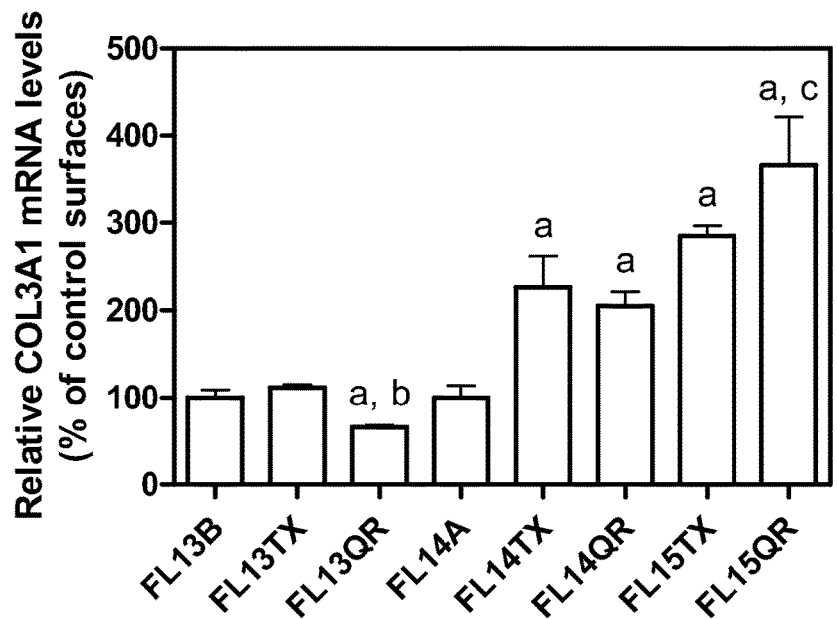
FIG. 12. Effect of the different surfaces on mRNA expression levels of COL3A1 in human gingival fibroblasts cultured for 14 days. Data were normalized to reference genes (beta-actin and GAPDH), expressed as percentage of control which was set to 100% (FL13B for FL13 groups; FL14A for FL14 and FL15 groups). Values represent the mean±SEM (N=6). Differences between groups were assessed by Student t-test: (a) p<0.05 versus control (FL13B for FL13 groups; FL14A for FL14 and FL15 groups); (b) p<0.05 differences between flavonoids in the same group; (c) p<0.05 FL14QR vs. FL15QR.

Real-time RT-PCR was performed to observe the effect of the different flavonoid-coated Ti surfaces on the expression of genes involved on extracellular matrix production and organization, regulation of cell adhesion and inflammation (FIGS. 11-12). Stability of the reference genes was assessed with the BestKeeper tool. The crossing point variation of the reference genes among samples was lower than 1.38. Moreover, a good consistence of the bestkeeper index was proved as its contributing reference genes were tightly correlated with it ($0.993<r<0.994$), with a significance level of $p=0.001$ for all reference genes.

Regarding the gene expression of the selected markers, mRNA levels of interleukin-6 (IL6), an inflammatory marker, were significantly lower in all flavonoid-coated surfaces compared with its controls without flavonoids (FIG. 11).

Surprisingly, COL3A1 increased only in all covalently-bonded flavonoid-coated groups compared with the silanized Ti/$TiO_2$ control (FL14A) and in quercitrin reduced Schiff base (FL15QR) compared with the non reduced surfaces (FL14QR). (FIG. 12)

Conclusions Example 2

None of the flavonoid-coated surfaces were toxic for HGF. After 24 hours of culture on the different surfaces, HGF possessed the typical fibroblastic spindle-shaped morphology and were distributed throughout the entire surface, without differences among the groups. This demonstrates that despite of the chemical modifications of the metallic surface of the implant by binding the linker and the flavonoid, toxicity has not been increased. Cytoskeleton and nuclei staining also revealed good cell spreading on all surfaces and the formation of prolongations and filopodia to contact each other and to attach to surfaces.

The different surface modification methods were effective in decreasing inflammation in HGF cells, as shown by the IL-6 mRNA levels. However, only flavonoids that were covalently attached to the implant surface were effective increasing the differentiation of HGF, as shown by the COL3A1 mRNA levels. Thus, to regenerate the gingival soft tissue around titanium implants with fibroblasts that are able to attach and differentiate (secreating collagen to the extracellular matrix), a coating that contains flavonoids covalently attached to the surface are prefered than those only physically adsorbed on the surface.

Example 3

Titanium Surfaces Functionalized with Flavonoids: Biocompatibility and Bioactivity on Human Umbilical Cord Mesenchymal Stem Cells Titanium surfaces were functionalized by drop casting and covalent linking (Schiff base and reduced Schiff base formation) as previously described in examples 1 and 2. Flavonoid release profiles from the different surfaces were also determined by UV-Vis spectroscopy. The biocompatibility and bioactivity of the different flavonoid-coated titanium surfaces were assessed in cell culture models of human umbilical cord mesenchymal stem cells (hUC-MSCs) differentiated to the osteogenic lineage, as a cell model for hard tissue around titanium implants. Cells cultured on flavonoid modified titanium surfaces were tested for cell toxicity, determined by LDH activity after 24 hours of incubation, cell morphology, determined by SEM and cytoskeleton and nuclei staining, and gene expression of differentiation markers after 14 days of culture.

Table 7 shows the different surfaces produced. Prior to flavonoid immobilization, passivation of machined titanium disks was carried out.

TABLE 7

Groups used in the study.

| Group | Modification |
|---|---|
| FL16B | Passivated, Ti/$TiO_2$ |
| FL16TX | Drop casting, Ti/$TiO_2$/Taxifolin |
| FL16QR | Drop Casting, Ti/$TiO_2$/Quercitrin |
| FL17A | Silanized Ti, Ti/$TiO_2$/APTES |
| FL17TX | Schiff base, Ti/$TiO_2$/APTES/Taxifolin |
| FL17QR | Schiff base, Ti/$TiO_2$/APTES/Quercitrin |
| FL18TX | Reduced Schiff base, Ti/$TiO_2$/APTES/Taxifolin |
| FL18QR | Reduced Schiff base, Ti/$TiO_2$/APTES/Quercitrin |

The flavonoid release profile was measured by UV-Vis spectroscopy as described in previous example, but in this case the aqueous media was changed at time 1 h, 1 day and 4, 7, 11 days, simulating hUC-MSCs culture media changes. Determination of citotoxicity, microscopic analysis of cell growth on the modified Ti surfaces and RNA isolation and real-time RT-PCR analysis was carried out as described in previous example. Primers used in the real-time PCR are detailed in table 8 and the function of genes selected as markers is explained in table 9.

TABLE 8

Primers used in the real-time PCR of reference and target genes. S: sense, A: antisense, bp: base pairs

| Gene | Primer sequence | Product size | GeneBank Accession Nr. |
|---|---|---|---|
| ALP | S: CCGCTATCCTGGCTCCGTGC<br>A: GGTGGGCTGGCAGTGGTCAG | 108 bp | NM_000478.3 |
| Coll-1 | S: CCTGACGCACGGCCAAGAGG<br>A: GGCAGGGCTCGGGTTTCCAC | 122 bp | NM_000088.3 |
| OC | S: GAAGCCCAGCGGTGCA<br>A: CACTACCTCGCTGCCCTCC | 70 bp | NM_199173 |
| Runx2 | S: GCCTTCAAGGTGGTAGCCC<br>A: CGTTACCCGCCATGACAGTA | 67 bp | NM_004348 |

TABLE 9

Function of selected genes.

| Gene | Function |
|---|---|
| ALP | Alkaline phosphatase is linked to phosphate metabolism and matrix maturation. It is one of the first functional genes expressed in the calcification process. |
| Coll-1 | Collagen type-1 is an early marker which supports cell differentiation stage. |
| OC | It is the most abundant non-collagenous protein in the bone and is implicated in bone mineralization and calcium ion homeostasis. Osteocalcin is normally used as a preliminary biomarker on the effectiveness of a given treatment on bone formation. |
| Runx2 | It is a key transcriptional factor involved in osteoblast differentiation. |

3.1. Cell Culture

Human umbilical cord derived mesenchymal stem cells (hUC-MSC) were isolated from umbilical cords obtained in the process of human umbilical cord blood donation under the Concordia Cord Blood Donation. The samples were obtained after informed consent and with the approval of the Ethical Committee of Balearic Islands (CEIC-IB). Once isolated, hUC-MSCs cells were routinely cultured at 37° C. in a humidified atmosphere of 5% $CO_2$. Cells were seeded at a density of $7.0 \times 10^3$ cells/well over the titanium coin-shaped implants and grown until confluence in a "growing media" consisting of DMEM-LG supplemented with penicillin (50 IU/mL), streptomycin (50 µg/mL) and 20% FBS (FB-1001, lot number 4253, Biosera, Boussens, France). At confluence (designated as day 0), cells were grown in "differentiation media" consisting of growing media supplemented with hydrocortisone (200 nM), ascorbic acid (50 µg/mL) and β-glycerophosphate (10 nM). Media was replaced twice weekly. Culture media was collected after 24 hours to test LDH activity. Some samples were processed by scanning electron microscopy and confocal microscopy to check cell morphology. Cells were harvested after 14 days to study gene expression.

Results 3.2. Flavonoid Release Profile by UV-Vis Spectroscopy

Figure 13:
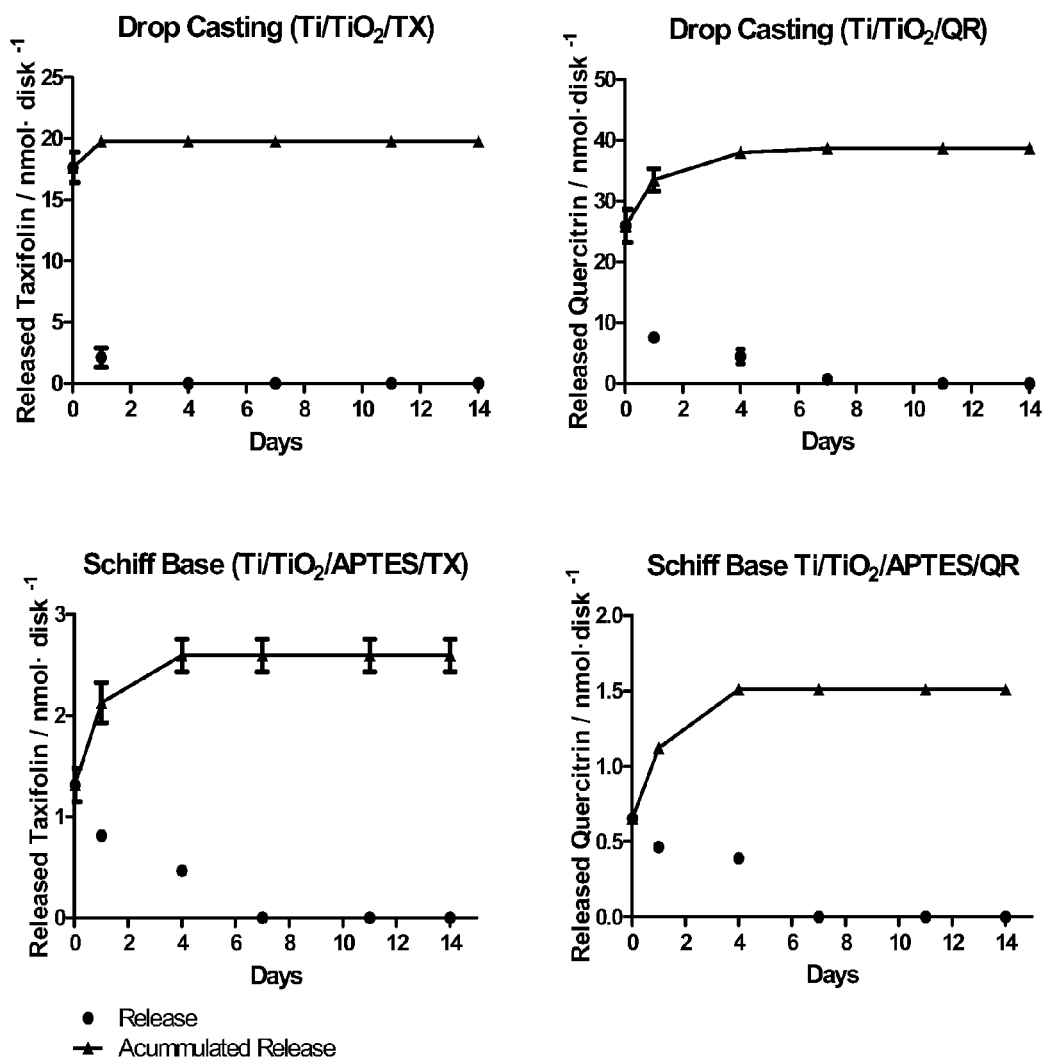
FIG. 13. Flavonoid release profile in aqueous media (pH 7.5, 37° C.) from samples coated by drop casting (top) and covalently linked by Schiff base formation (bottom) simulating hUC-MSCs culture media changes. Left: taxifolin coated substrates, right: quercitrin coated.

FIG. 13 shows the flavonoid release profile from flavonoid-coated Ti disks in aqueous media up to 14 days, simulating physiologic conditions (pH 7.5, 37° C.), from drop casted (experiment FL16) and covalently linked by Schiff base formation (experiment FL17) samples.

Drop Casted substrates. The initial flavonoid amount deposited on the Ti surface by drop casting was 20 nmol/disk for taxifolin implants and 50 nmol/disk for quercitrin. For both drop casted surfaces the maximum release took place within the first hour of sample incubation. The total taxifolin amount released to media was 19.7±0.7 nmol. The total quercitrin amount released represented a 78% of the expected value (39 nmol vs 50 nmol).

Covalently linked subtrates. FIG. 13 also shows the release profile of Ti surfaces functionalized with taxifolin and quercitrin by Schiff base formation (experiment FL17). In this experiment, the Schiff bases obtained were not reduced. Therefore the C=N bond supposedly formed between the $NH_2$ terminated surface and the carbonyl group of the flavonoid should be reversible, and the flavonoid might be released from the substrate. Taxifolin and quercitrin release from Schiff base surfaces were similar. The total amount of taxifolin released after 14 days was 2.6±0.2 nmol. By the other hand, the total amount of quercitrin released after 14 days was 1.51±0.04 nmol. In both cases the maximum released amount took place within the first hour of incubation and the release was complete between 1 and 4 days of incubation.

No taxifolin neither quercitrin were detected in the media from reduced Schiff base surfaces (experiment FL18). This agrees with the expected formation of an irreversible stable bond between the flavonoid and the APTES/Ti surface.

3.3. Biocompatibility of Flavonoid-Coated Titanium Surfaces with Human Umbilical Cord Mesenchymal Stem Cells.

Figure 14:
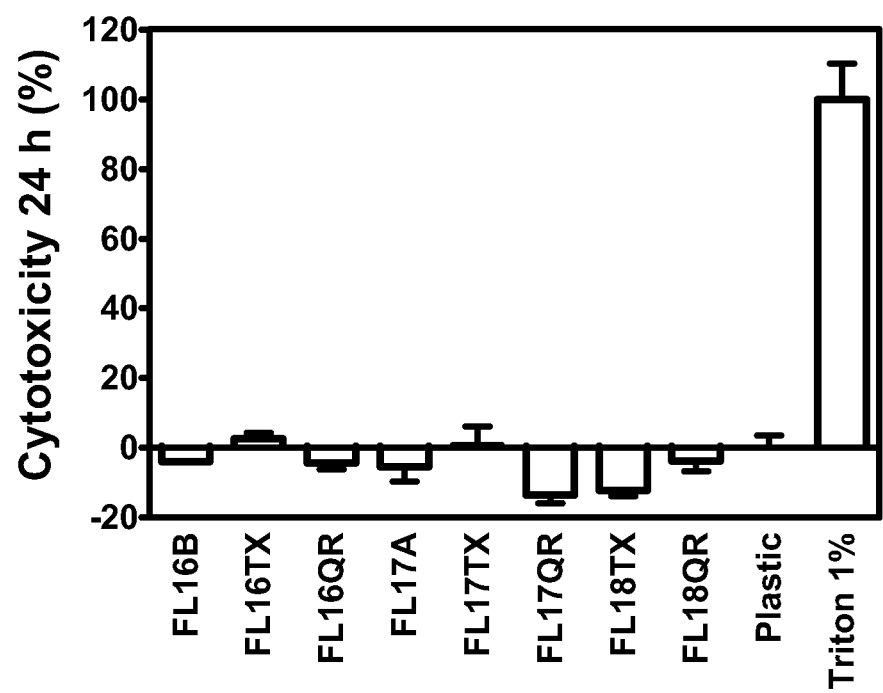
FIG. 14. LDH activity measured in culture media collected after 48 hours of treatment in human gingival fibroblasts. High control (100% cytotoxicity) was cell culture media from cells treated with 1% Triton X-100. Low control (0% cytotoxicity) was cell culture media from control vehicle cells. The percentage of LDH activity was calculated using the following equation: Cytotoxicity (%)=(exp.value–low control)/(high control–low control)*100. Values represent the mean±SEM (N=6).

Cytotoxicity of treatments was evaluated by measuring the release of LDH from hUC-MSCs to the culture media after 24 hours of treatment (FIG. 14). None of the surfaces were toxic for these cells and no significant differences were found when comparing the flavonoid-coated groups with its controls.

3.4. Effect of the Different Flavonoid-Coated Titanium Surfaces on Cell Morphology.

Figure 15:
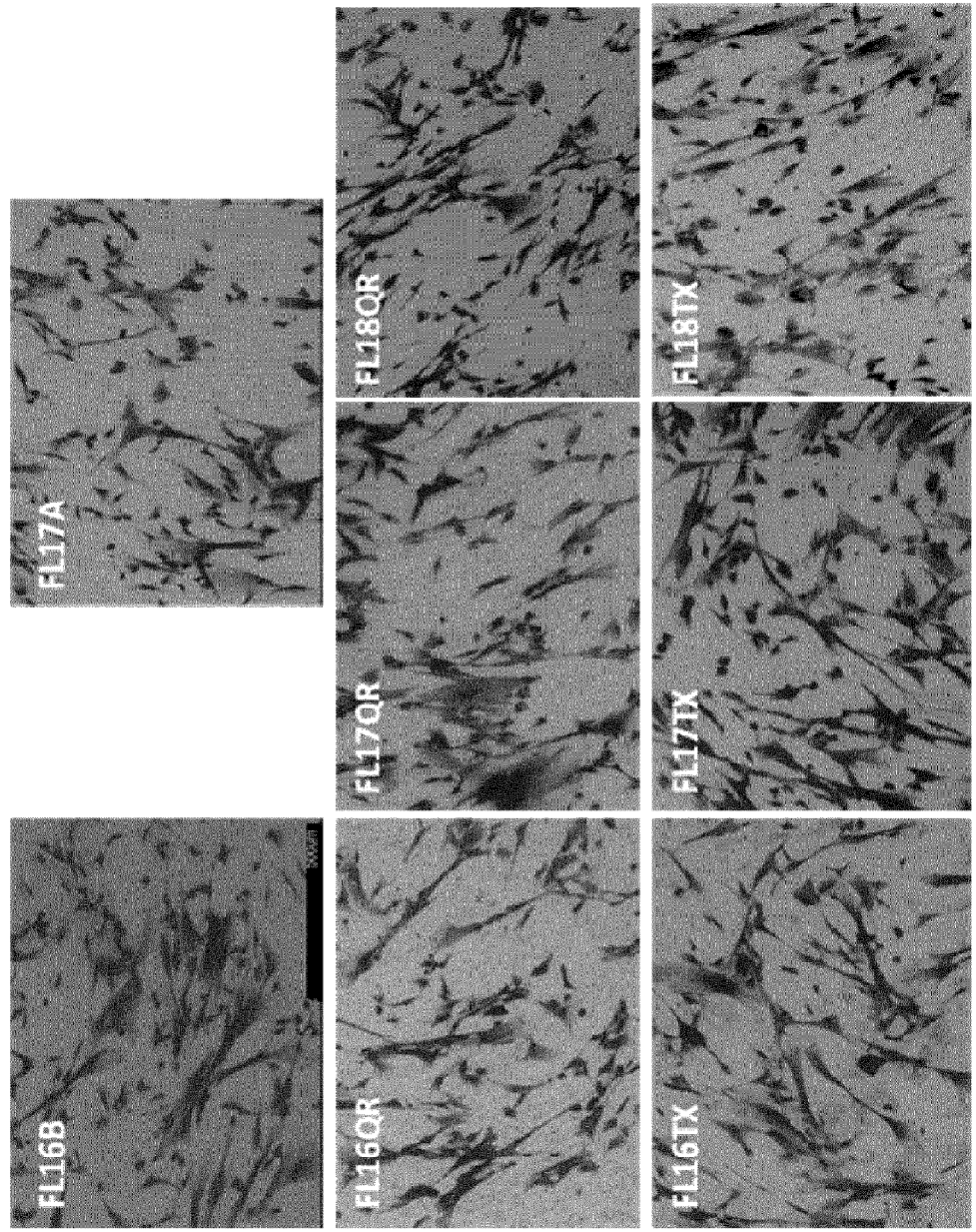
FIG. 15. Scanning electron microscope micrographs of human umbilical mesenchymal stem cells on the different surfaces. Scale bar=500 μm.
Figure 16:
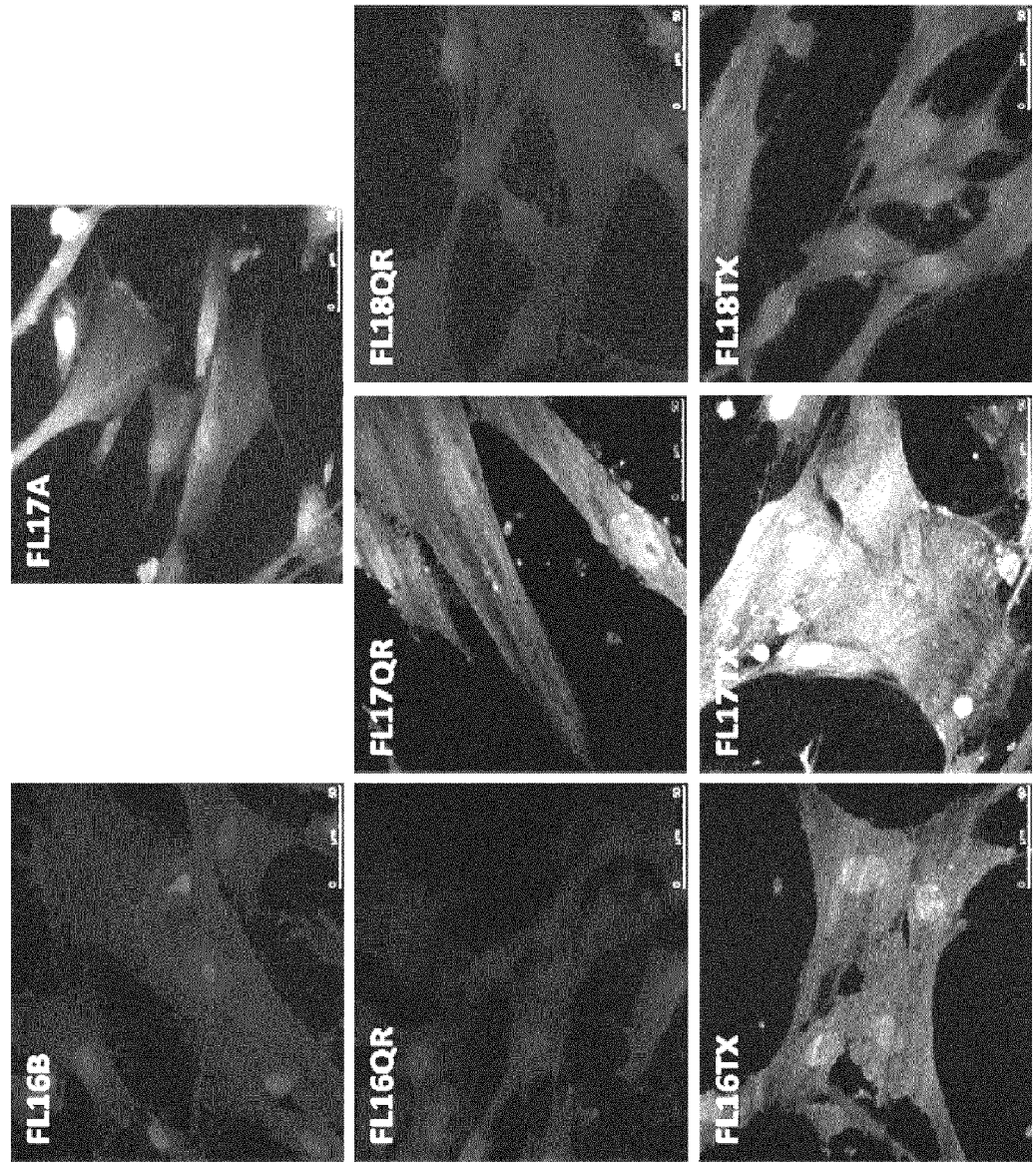
FIG. 16. Cytoskeleton and nuclei immunostaining of human umbilical mesenchymal stem cells on the different surfaces. Scale bar=50 μm.

After 24 hours of culture on the different surfaces, hUC-MSCs showed the typical morphology with long thin cell bodies and prominent nucleous which were placed throughout the entire surface, without differences among the groups (FIGS. 15 and 16).

3.5. Effect of the Different Flavonoid-Modified Surfaces on Gene Expression.

Figure 17:
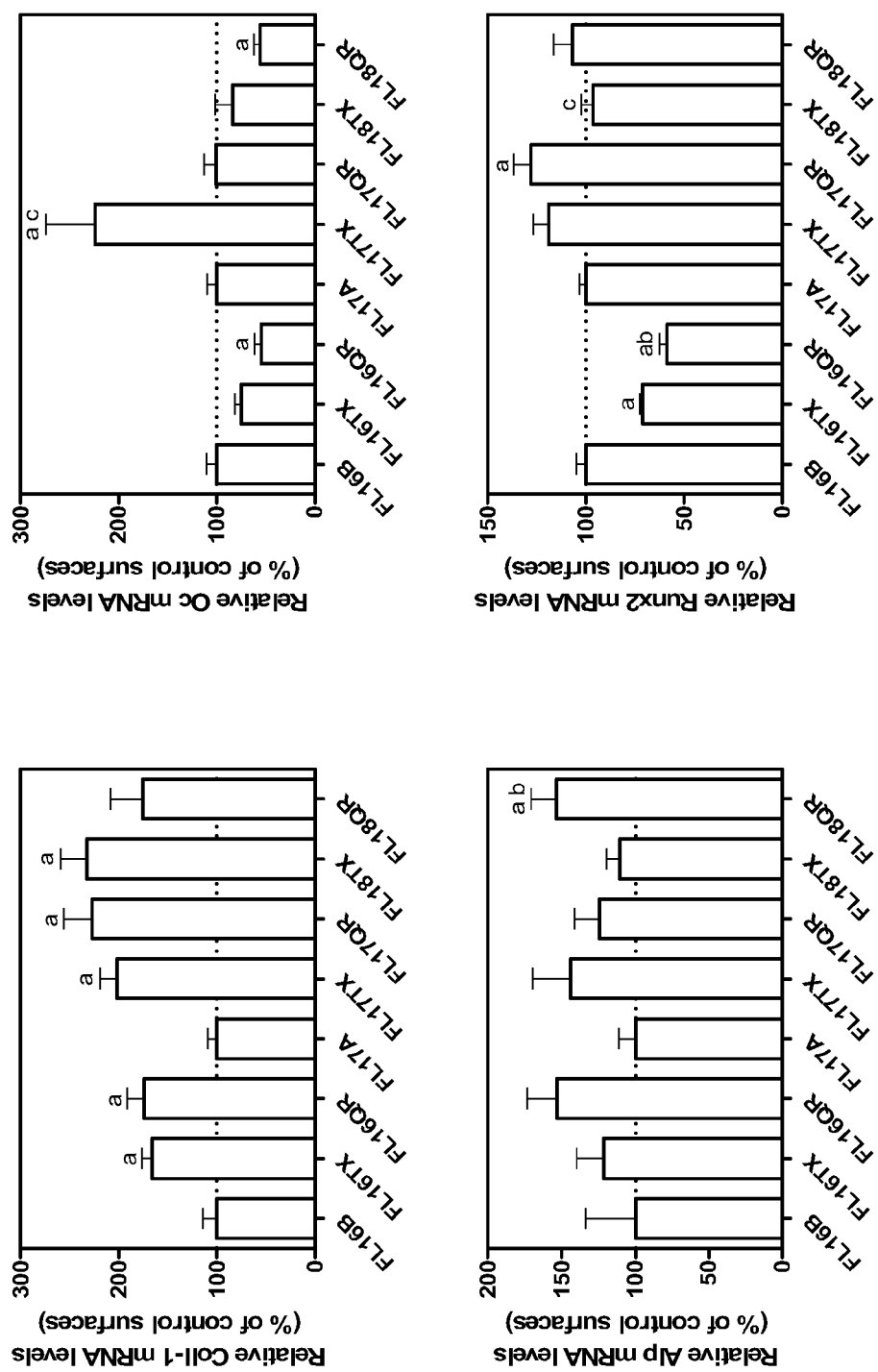
FIG. 17. Effect of the different surfaces on mRNA expression levels of Coll-1, Oc, Alp and Runx2 in human umbilical mesenchymal stem cells cultured for 14 days. Data were normalized to reference genes (beta-actin and GAPDH), expressed as percentage of control which was set to 100% (FL16B for FL16 groups; FL17A for FL17 and FL18 groups). Values represent the mean±SEM (n=6). Differences between groups were assessed by Student t-test: (a) p<0.05 versus control (FL16B for FL16 groups; FL17A for FL17 and FL18 groups); (b) p<0.05 differences between flavonoids in the same group; (c) p<0.05 differences between groups for the same flavonoid.

Real-time RT-PCR was performed to observe the effect of the different flavonoid-coated Ti surfaces on the expression of genes involved on osteoblast differentiation, matrix maturation and mineralization (FIG. 17). Stability of the reference genes was assessed with the BestKeeper tool. The crossing point variation of the reference genes among samples was lower than 0.35.

Moreover, a good consistence of the bestkeeper index was proved as its contributing reference genes were tightly correlated with it (0.879<r<0.900), with a significance level of p=0.001 for all reference genes.

Regarding the gene expression of the selected markers (FIG. 17), mRNA levels of Collagen type-1 (Coll-1) were significantly higher in all flavonoid-coated surfaces compared with its controls without flavonoids. The expression of osteocalcin (OC) was significantly decreased in cells cultured on quercitrin drop casted surfaces (FL16QR) and in cells cultured on quercitrin reduced Schiff base surfaces (FL18QR) compared with their corresponding controls. However, cells cultured over taxifolin Schiff base samples (FL17TX) revealed a higher OC expression compared with its control and with the taxifolin reduced Schiff base (FL18TX). Regarding to the alkaline phosphatase gene expression (ALP), quercitrin reduced Schiff base (FL18QR) was the only treatment showing an increase in ALP levels compared with its control and with taxifolin reduced surfaces (FL18TX). Finally, Runx2 mRNA expression was statistically higher in quercitrin Schiff base group (FL17QR) compared with its control whereas it decreased in taxifolin and quercitrin drop casted surfaces (FL16TX, FL16QR) compared with the control (FL16B). Significant differences were also observed in Runx2 gene expression for quercitrin drop casted samples (FL16QR) compared with taxifolin drop casted (FL16TX) and for taxifolin reduced Schiff base (FL18TX) compared with the non reduced taxifolin group (FL17TX).

Conclusions Example 3

None of the surfaces was toxic for hUC-MSCs. After 24 hours of culture on the different surfaces, hUC-MSCs showed the typical morphology with long thin cell bodies and prominent nucleous, which were placed throughout the entire surface, without differences among the groups.

As regards to the differentiation profile of the hUC-MSCs, cells cultured on implants that had flavonoids covalently attached showed superior differentiation than cells cultured on flavonoid drop-casted implants, as shown by the higher collagen-1, osteocalcin and, more importantly, runx2. Runx2 is a master organizer of gene transcription in developing and maturing osteoblasts, which are the main cells in hard tissue supporting osseointegrated implants.

Example 4

Figure 18:
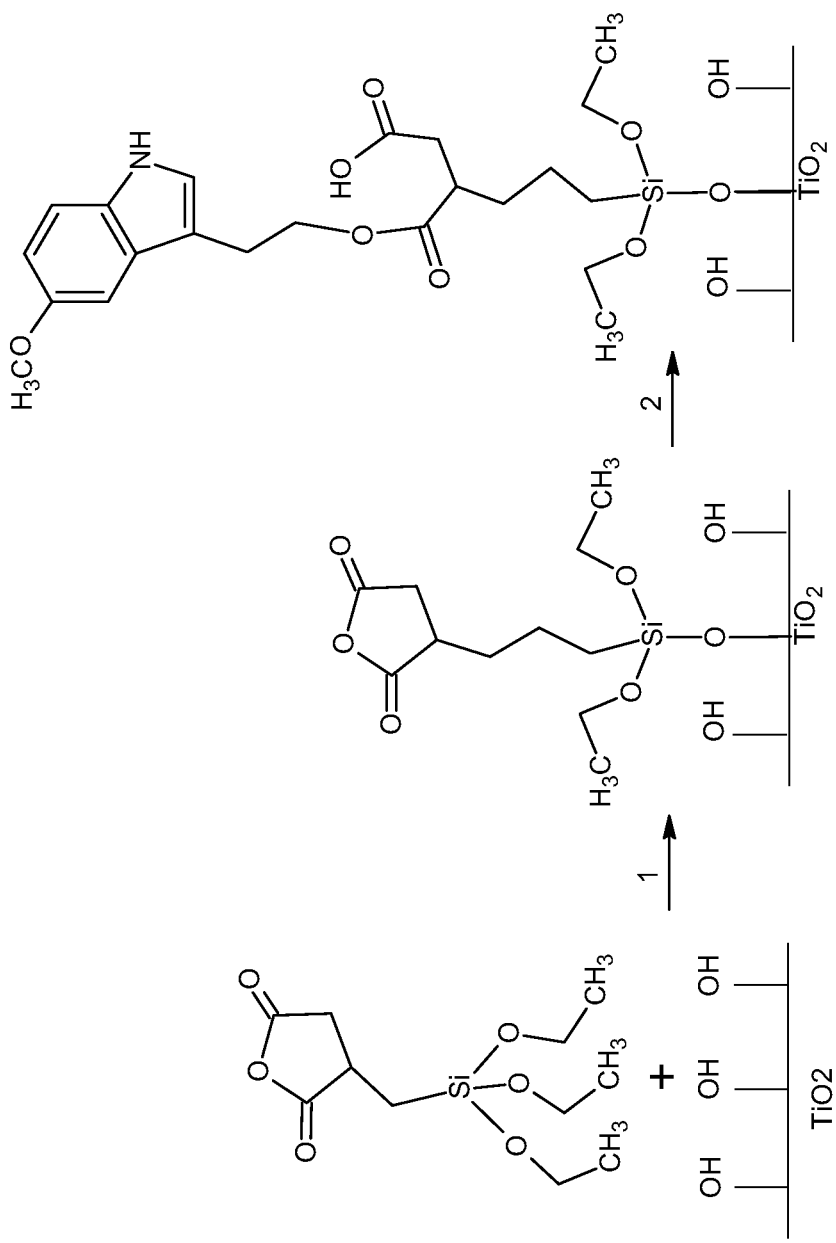
FIG. 18. Covalent immobilization of 5-methoxytryptophol on $Ti/TiO_2$ substrates. (1) Reaction of the pretreated $Ti/TiO_2$ surface with triethoxysilylpropyl succinic anhydride (TESPSA). (2) Reaction of the hydroxyl group of 5-methoxytryptophol with the acid anhydride group of the silane to form an ester.

Covalent Immobilization Of 5-Methoxytryptophol On Titanium Surfaces 5-methoxytryptophol (5-MTX) can be covalently immobilized to pretreated Ti surfaces through an esterification reaction. A coupling agent with a carboxylic, acid anhydride or acyl chloride functionality can react with the hydroxyl moiety of 5-MTX to give an ester (FIG. 18).

Acid anhydride functionalization of Ti surfaces can be carried out by using triethoxysilylpropyl succinic anhydride (TESPSA) as a crosslinker. TESPSA is a silane, structurally similar to APTES but with a succinic anhydride end instead of an amine. Hydrolysis of the anhydride will give the carboxylic acid functionality, which is also reactive towards hydroxyl esterification although in a slower manner than the acid anhydride.

4.1. Procedure of Covalent Immovilization.

Prior to the functionalization, activation of the Ti surface by UV irradiation or passivation is carried out, as described in Example 1.

The silanization of the Ti/TiO$_2$ substrates with TESPSA was carried out in anhydrous conditions to avoid hydrolysis of the succinic anhydride moiety of TESPSA. Immediately after Ti pretreatment, the implants were immersed in a 10% v/v TESPSA solution in dry toluene for 24 h at room temperature. Anhydrous MgSO$_4$ was added to scavenge the water formed from the condensation of the etoxy groups of the silane with the hydroxilated Ti surface. Then rinse gently with dry toluene.

For the immobilization of 5-MTX, a solution of 1 mM 5-MTX in dry toluene was prepared and anhydrous MgSO$_4$ or molecular sieves 4A was added. The silanized disks were immersed in the 5-MTX solution, few drops of concentrated H$_2$SO$_4$ to catalyze the esterification were added, and the final solution was stirred for 1 h at RT. Finished this time, disks were rinsed gently with dry toluene, DMSO and water at pH 7 and dried with N$_2$.

Example 5

Functionalization of Titanium Surfaces With 5-Methoxytryptophol by Drop Casting This example shows how titanium surfaces can be homogeneously coated with 5-methoxytryptophol by a drop casting procedure.

5.1. Reagents and Methods

Machined titanium coins were cleaned and passivated as described in Example 1. Immediately after Ti passivation, a 5 µl drop of a 10 mM 5-methoxytryptophol solution in ethanol was added to each coin and the solution was left to air dry for 30 min. FTIR-ATR coupled to optical microscopy analysis of the surfaces were carried out as described in Example 1. FTIR spectra of pure, solid 5-methoxytryptophol was obtained with an ATR accessory.

Figure 19:
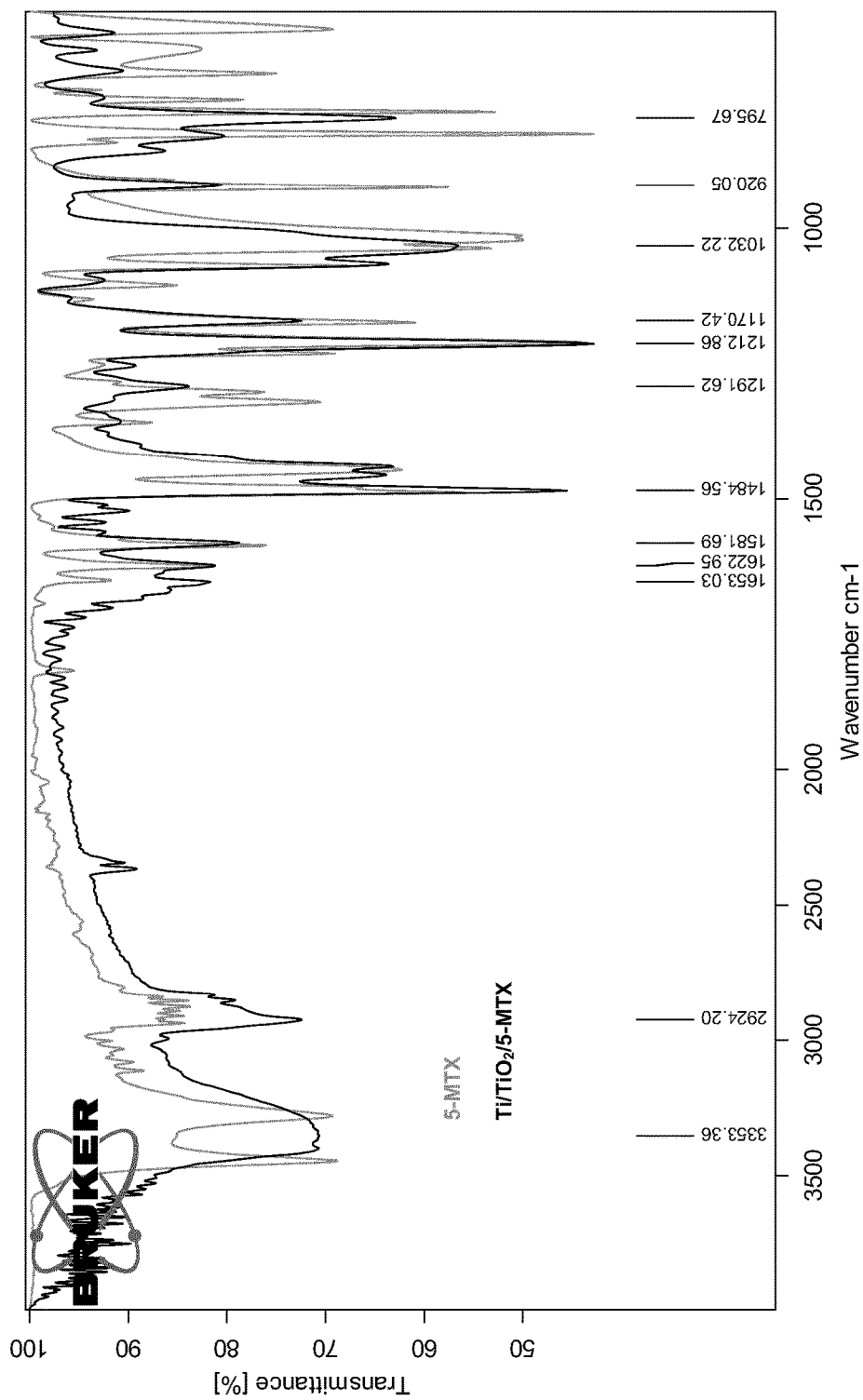
FIG. 19. Comparison of FTIR-ATR average spectra of $Ti/TiO_2$ samples coated by drop casting with 5-methoxytryptophol, with the spectrum of the pure compound. Each spectrum corresponds to the average of at least ten measurement points along the implant surface.

Results FTIR analysis of the coated surfaces showed the presence of the biomolecule homogenously distributed along the surface (FIG. 19).

CONCLUSION

Titanium metal surfaces can be homogeneously coated with 5-methoxytryptophol using drop casting methods.

The invention claimed is:

1. A biocompatible implant for improved osseointegration and soft tissue attachment when implanted into a mammalian body, comprising a combination of:
one or more metal(s), metal alloy(s), metal oxide(s) or a combination thereof, the one or more metal(s), metal alloy(s), metal oxide(s) or a combination thereof having at least one surface, and,
a coating containing a methoxytryptophol or flavonoid compound either directly attached to the at least one surface by a covalent bond, or attached through an optional linker;
wherein the methoxytryptophol or flavonoid compound is selected from the group of flavonoids, methoxytryptophols, an ester thereof, a pharmaceutically acceptable salt thereof, and a combination thereof,
wherein the methoxytryptophol or flavonoid compound is/are coated to at least a part of the surface of the metal, metal alloy or metal oxide of said biocompatible implant,
wherein the methoxytryptophol or flavonoid compound is covalently attached to the surface of the metal, metal alloy or metal oxide so that either
the methoxytryptophol or flavonoid compound is directly attached to the one or more of the metal, metal alloy or metal oxide forming a covalent bond therewith, or
the methoxytryptophol or flavonoid compound is bound to the surface of the one or more of the metal, metal alloy or metal oxide through the optional linker forming a covalent bond between the methoxytryptophol or flavonoid compound and the linker and between the linker and the one or more of the metal, metal alloy or metal oxide; and
wherein the linker is selected from the group of one or more of anhydrides, alcohols, acids, amines, epoxides, isocyanates, silanes, thiol, alkyl, aryl, and halogenated groups; and
whereby the combination is configured to provide improved osseointegration and soft tissue attachment when implanted into a mammalian body.

2. The biocompatible implant according to claim 1, wherein the flavonoid compound comprises at least one carbonyl group.

3. The biocompatible implant according to claim 2, wherein the flavonoid is selected from quercitrin, taxifolin, galangin, diosmetin, chrysin or derivatives thereof.

4. The biocompatible implant according to claim 1, wherein the methoxytryptophol compound is selected from 5-methoxytryptophol or 6-methoxytryptophol.

5. The biocompatible implant according to claim 1 wherein the linker is a silane.

6. The biocompatible implant according to claim 5 wherein the silane is selected from 3-aminopropyltriethoxysilane or triethoxysilanepropylsuccinic acid.

7. The biocompatible implant according to claim 1 wherein the linker is a polyether.

8. The biocompatible implant according to claim 7, wherein the polyether is polyethilenglycol or its derivatives.

9. The biocompatible implant according to claim 1, wherein said metal(s), metal alloy(s) or metal oxide(s) is/are selected from titanium, an alloy or an oxide thereof, zirconium, an alloy or an oxide thereof, tantalum, an alloy or an oxide thereof, hafnium, an alloy or an oxide thereof, niobium, or an alloy or an oxide thereof, chromium-vanadium alloy and stainless steel.

10. The biocompatible implant according to claim 9 wherein said metal, metal alloy or metal oxide is titanium.

11. The biocompatible implant according to claim 1, wherein the implant is selected from a surgical implant, an orthopedic implant, a dental implant, an orthopedic fixation device, an orthopedic joint replacement, a prosthetic disc for spinal fixation, a graft material.

12. The biocompatible implant according to claim 1, wherein the implant comprises a metal oxide scaffold comprising titanium oxide.

13. A biocompatible implant for improved osseointegration and soft tissue attachment when implanted into a mammalian body, comprising a combination of:
one or more metal(s), metal alloy(s), metal oxide(s) or a combination thereof, the one or more metal(s), metal alloy(s), metal oxide(s) or a combination thereof having at least one surface, and
a coating containing a methoxytryptophol or flavonoid compound either directly attached to the at least one surface by a covalent bond, or attached through an optional linker;
wherein the methoxytryptophol or flavonoid compound is selected from the group of flavonoids, methoxytryptophols, an ester thereof, a pharmaceutically acceptable salt thereof, and a combination thereof,
wherein the methoxytryptophol or flavonoid compound is/are coated to at least a part of the surface of the metal, metal alloy or metal oxide of said biocompatible implant, wherein the methoxytryptophol or flavonoid compound is covalently attached to the surface of the metal, metal alloy or metal oxide so that either the methoxytryptophol or flavonoid compound is directly attached to the one or more of the metal, metal alloy or metal oxide forming a covalent bond therewith, or the methoxytryptophol or flavonoid compound is bound to the surface of the one or more of the metal, metal alloy or metal oxide through the optional linker forming a covalent bond between the methoxytryptophol or flavonoid compound and the linker and between the linker and the one or more of the metal, metal alloy or metal oxide; and wherein the linker is selected from the group of one or more of anhydrides, alcohols, acids, amines, epoxides, isocyanates, silanes, thiol, alkyl, aryl, and halogenated groups; and whereby the combination is configured to provide improved osseointegration and soft tissue attachment when implanted into a mammalian body; and wherein further biomolecules are present on the surface of the metal, metal alloy or metal oxide of the implant, said biomolecules being selected from natural biomolecules, synthetic biomolecules, and recombinant biomolecules, cell attachment factors, biopolymers, blood proteins, enzymes, extracellular matrix proteins and biomolecules, growth factors and hormones, nucleic acids, receptors, synthetic biomolecules, vitamins, drugs, biphosphonates, biologically active ions, and marker biomolecules.

14. A method for producing a biocompatible implant according to claim 1, comprising reacting an antioxidant compound as defined in claim 1 with the surface of said biocompatible implant.

15. The method according to claim 14, comprising: a) chemically pre-treating the surface of an implant b) reacting a linker with said chemically pre-treated surface obtained in the pre-treating operation hereof, and c) reacting an antioxidant compound selected from the group of flavonoids, methoxytryptophols, an ester thereof, a pharmaceutically acceptable salt thereof, and a combination thereof, with said linker.

16. The method according to claim 14, comprising: a) chemically pre-treating the surface of an implant b) reacting a linker with the antioxidant compound, wherein the antioxidant compound is selected from the group of flavonoids, methoxytryptophols, an ester thereof, a pharmaceutically acceptable salt thereof, and a combination thereof, and c) reacting the antioxidant-linker conjugate thus obtained, with said pretreated surface obtained in the pre-treating operation hereof.

17. The method according to claim 14, further including reacting an antioxidant compound with a linker, wherein after reacting the antioxidant compound with the linker, a reduction is performed.

18. The method according to claim 17 wherein the reduction is carried out with sodium cyanoborohydride.

19. The method according to claim 14, further including a pre-treatment of the surface of an implant, wherein the pretreatment step-is selected from piranha attack, passivation, UV irradiation, acid or alkaline attack.

20. A method to replace bone tissue and/or restore a function of the body of a vertebrate animal comprising implanting the biocompatible implant according to claim 1, in particular a mammal, such as a human.

* * * * *